United States Patent [19]

Oonishi et al.

[11] Patent Number: 5,223,029
[45] Date of Patent: Jun. 29, 1993

[54] HARDENING MATERIAL FOR MEDICAL AND DENTAL USE

[75] Inventors: Hironobu Oonishi, Osaka; Fumihito Sugihara, Kishiwada; Takashi Ishii, Osaka; Kaneo Suzuki, Kashihara; Seiko Hata, Osaka; Toshikazu Takano, Nara, all of Japan

[73] Assignee: Nitta Gelatin Inc., Osaka, Japan

[21] Appl. No.: 477,864

[22] PCT Filed: Jun. 22, 1989

[86] PCT No.: PCT/JP89/00620
§ 371 Date: Apr. 9, 1990
§ 102(e) Date: Apr. 9, 1990

[87] PCT Pub. No.: WO90/01341
PCT Pub. Date: Feb. 22, 1990

[30] Foreign Application Priority Data
Aug. 10, 1988 [JP] Japan .................. 63-200617

[51] Int. Cl.⁵ .............. C09K 3/00; C08L 89/00
[52] U.S. Cl. .................... 106/35; 106/124; 106/137
[58] Field of Search ............ 106/35; 501/1,6

[56] References Cited

U.S. PATENT DOCUMENTS

| | | | |
|---|---|---|---|
| 4,524,824 | 6/1985 | Shimokobe et al. | 106/35 |
| 4,608,088 | 8/1986 | Lokken | 106/35 |
| 4,776,890 | 10/1988 | Chu | 106/161 |
| 4,865,602 | 9/1989 | Smestad et al. | 623/16 |
| 5,001,169 | 3/1991 | Nathan et al. | 523/113 |

FOREIGN PATENT DOCUMENTS

| | | |
|---|---|---|
| 58-183607 | 10/1983 | Japan . |
| 60-36404 | 2/1985 | Japan . |
| 62-12705 | 1/1987 | Japan . |
| 62-72363 | 4/1987 | Japan . |
| 62-83348 | 4/1987 | Japan . |
| 63-115567 | 5/1988 | Japan . |
| 63-153070 | 6/1988 | Japan . |

*Primary Examiner*—Mark L. Bell
*Assistant Examiner*—Margaret Einsmann
*Attorney, Agent, or Firm*—Armstrong, Westerman, Hattori, McLeland & Naughton

[57] ABSTRACT

This invention relates to a hardening material for medical and dental use, in which at least either one or both of α-tricalcium phosphate and tetracalcium phosphate as an essential component and, as a hardening adjuster, the following ① tannin, ② tannin and collagen, ③ collagen and an organic acid, ④ tannin, collagen, and an organic acid, ⑤ tannin and an organic acid, or ⑥ at least two kinds or organic acids.

8 Claims, 18 Drawing Sheets

HARDENING MATERIAL FOR MEDICAL AND DENTAL USE

TECHNICAL FIELD

This invention relates to hardening materials for medical and dental use (hereinafter simply referred to as "hardening material") which may be used for a bone cement, a cement for dental use, and root canal sealing material.

BACKGROUND ART

In recent years, cements for dental use have contained hydroxyapatite (hereinafter referred to as "HAp and α-tricalcium phosphate [α-$Ca_3(PO_4)$α-$Ca_3(PO_4)_2$: hereinafter referred to as "α-TCP"] powder and an aqueous solution of polyacrylic acid as a setting solution. A hardened product is made by mixing, and kneading of the powder with the setting solution. However, polyacrylic acid, which does not react during the hardening, sometimes remains and thus, there exists a problem that a body may suffer damage due to elusion of the acid.

Also, for cements for dental use and root canal sealing materials, there have been known cement and root canal sealers in a series of zinc oxide eugenol in which eugenol is mixed to a setting liquid with a purpose of a pain-killing effect. However, cell toxicity has been reported with eugenol and also, a composite resin, that is a material for recovery of a tooth crown part, is disturbed by polymerization with eugenol. Therefore, a number of problems exist for the materials in the eugenol series for dental use.

There has been marketed a bone cement in which a polymer material such as polymethylmethacrylate (PMMA) and methylmethacrylate (MMA) is used. However, the following three problems have been known for this bone cement in which a polymer material is used. First, a bone tissue in a host, which is subjected to plugging up, does not directly combine with the bone cement and, when the bone cement is plugged up in a living body for a long period, there exists a problem such as loosening due to interposition of a fibril tissue. Second, since the temperature is raised to 90°~100° C. with heat-generation during hardening, there exists a problem that surrounding cells are killed. Third, there exists a problem that elution of a monomer or an oligomer which has not reacted creates a bad effect on the bone.

On the other hand, there have been proposed a number of hardening materials which are furnished with α-TCP powder or tetracalcium phosphate powder ($Ca_4(PO_4)_2$ 0: hereinafter referred to as "4CP"), which are substances analogous to HAp that is a main inorganic component of body hard tissue, and also furnished with a setting liquid composed of a solution of a type of organic acid. For example, in Japanese official patent provisional publication of Showa 60-36404, there is described a material furnished with α-TCP powder and a setting solution of 1 M tannic acid. In Japanese official patent provisional publication of Showa 62-12705, there is described a material furnished with α-TCP powder and a 30~60% (w/w) aqueous solution of citric acid. Also, in Japanese official patent provisional publication of Showa 62-83348, there is described a material furnished with α-TCP powder and a 45% (w/w) aqueous solution of hydroxysuccinic acid. The α-TCP and 4CP are of high chemical reactivity and can be converted into HAp under the conditions similar to those in a body or a mouth.

The hardening materials described in the above publications have properties such that they cause almost no damage to a body, have the capability to form a hardened product analogous to body hard tissue, and have the capability to combine with hard tissue. A hardening material furnished with α-TCP or 4CP as a powder component and with a solution of an organic acid as a setting liquid component is very useful for medical and dental use, so that its practical use is very acceptable.

The hardening materials and their hardened products cause no damage to a body, but if a ratio between calcium phosphate powder and the setting solution (hereinafter simply referred to as "powder: liquid ratio") becomes large, the time for hardening becomes extremely short, so that there exists a problem that practical use is not possible.

Hardening materials are classified, for example, in the undermentioned major two classes (a) and (b).

(a) Sealing agent . . . The applications for use are the ones where a very great force does not operate, and the agent is used for plugging up and blocking up a gap or as a firmly fixing supporter, and the time for hardening of the agent is very long. The agent does not show high values in properties of the hardening materials, especially, in resisting force against crushing and it is preferred if the agent slowly releases a substance which has a pain-killing effect. For example, it is used as a bone sealer or a root canal sealer, etc.

(b) Cement . . . The applications for use are ones where a definite weighing force operates, and the agent is used for plugging up and blocking up a gap or with a purpose of joining of hard body tissues to one another, joining a hard body tissue to other material, or between other materials themselves. When a user is going to mix and knead the agent, the time for hardening is properly short and thus, the hardening proceeds in relatively short time, and after hardening, the agent shows a definitely high value in material properties, especially in resisting force against crushing and it is preferred if it could firmly make a chemical bond with a hard body tissue. The examples are bone cement, cement for dental use, and an adhering agent for dental use.

According to the above considerations, the present invention has an object to provide a hardening material which can be applied as the sealer described in the above class (a) and/or the cement described in class (b), undergoes hardening at about room temperature or body temperature, has no injurious character for a body, and besides, has properties of formation of a hardened product analogous to a hard body tissue and the joining with a hard body tissue, and also whose time for hardening is freely controlled without lowering the working efficiency for mixing and kneading.

DISCLOSURE OF THE INVENTION

The hardening material relating to the present invention is firstly characterized by that, to solve the above-described objects, calcium phosphate powder containing at least one of α-TCP 4CP is involved as an essential component and, at least one compound selected from tannin or tannin derivatives is used as a hardening adjuster.

The hardening material relating to the present invention is secondly characterized by that, to solve the above-described objects, calcium phosphate powder containing at least one of α-TCP and 4CP is involved as an essential component and, at least one compound selected from tannin and tannin derivatives and at least one compound from collagen and collagen derivatives are used as a hardening adjuster.

The hardening material relating to the present invention is thirdly characterized by that, to solve the above-described objects, calcium phosphate powder containing at least one of α-TCP and 4CP is involved as an essential component and, at least one compound selected from collagen and collagen derivatives and one kind or more of organic acid are used as a hardening adjuster.

The hardening material relating to the present invention is fourthly characterized by that, to solve the above-described objects, calcium phosphate powder containing at least one of α-TCP and 4CP is involved as an essential component and, at least one compound selected from tannin and tannin derivatives, at least one compound from collagen and collagen derivatives, and one kind or more of organic acid are used as a hardening adjuster.

The hardening material relating to the present invention is fifthly characterized by that, to solve the above-described objects, calcium phosphate powder containing at least one of α-TCP and 4CP is involved as an essential component and, at least one compound selected from tannin and tannin derivatives and one kind or more of organic acid are used as a hardening adjuster.

Furthermore, the hardening material relating to the present invention is sixthly characterized by that, to solve the above-described objects, calcium phosphate powder containing at least one of α-TCP and 4CP is involved as an essential component and, at least two kinds of organic acid are used as a hardening adjuster.

Hereinafter, the present invention is explained in detail.

The hardening material relating to the present invention is composed of combination of, at least, calcium phosphate powder and a setting liquid.

At least either one of α-TCP and 4CP takes a part or a whole of the calcium phosphate powder. A residual part of the powder is taken by HAp, apatite carbonate, β-tricalcium phosphate (hereinafter referred to as "β-TCP"), and calcium hydrogen phosphate dihydrate etc. The calcium phosphate powder is, in a preferred case, 4CP in its 10~100% (w/w), α-TCP in 0~90% (w/w), and HAp in 0~30% (w/w). If 4CP is less than 10% (w/w) of the calcium phosphate powder, there may take place such a problem that, after mixing and kneading, the physical strength of a hardened product becomes extremely low. If HAp is more than 30% (w/w) of the calcium phosphate powder, the time for hardening becomes short and there may take place such a problem that mixing and kneading is not enough. The 4CP is more reactive than α-TCP, thereby the pot life becomes short and handling becomes difficult and thus, suppression of its reactivity is carried out by adding α-TCP. Also, in the calcium phosphate powder it is preferred that the 60 ~100% (w/w) is α-TCP and the 0~30% (w/w) is HAp. In a case of that α-TCP is less than 60% (w/w) of the calcium phosphate powder, there may take place a problem that, after mixing and kneading, the physical strength of the hardened product becomes extremely low. If the calcium phosphate other than α-TCP and HAp is more than 10% (w/w) of the powder, the hardening may be insufficient, or there may take place a problem that the time for hardening becomes short and the mixing and kneading cannot be performed sufficiently. Furthermore, the components other than 4CP, α-TCP, and HAp are preferred to be 40% (w/w) or less of the calcium phosphate powder. If these components exceed this percentage, the physical strength of the mixed and kneaded, hardened product may become extremely low.

Also, if a powder other than said calcium phosphate does not disturb the reaction, replacement by 30% (w/w) of the total powder agent is possible with this powder. The powder other than calcium phosphate is, for example, a barium salt, a bismuth salt, a zinc salt, and these oxides, which are for addition of a X-ray contrast character, or a dye such as β-carotin, a pigment such as titanium dioxide, or a fluoride such as calcium difluoride. So long as the powder does not participate in a reaction or does not give adverse effects on the physical properties, all kinds of powder which are replaceable with a purpose other than these are concerned.

The powder is preferred if it has an average particle diameter of 1~24 μm. If the average particle diameter of the powder is less than 1 μm, there may take place a problem that, although physical strength of the hardened product increases, the time for hardening becomes short. If it is more than 25 μm, especially in a case of that it is used for cement for dental use, there sometimes takes place a problem that the film thickness of the hardened product does not become 30 μm or less.

The 4CP is obtained, for example, by baking followed by pulverizing a composition of $\tau$-$Ca_2P_2O_7$ and $CaCO_3$ in a 1:2 molar ratio at a temperature of 1300° C. or more, but also 4CP obtained from other methods can be used. The α-TCP is obtained, for example, by baking followed by pulverizing a composition of $\tau$-$Ca_2P_2O_7$ and $CaCO_3$ in an equal molar ratio at a temperature of 1200° C. or more, but also α-TCP obtained from other methods can be used. The HAp etc. may be calcium phosphate originated from a living body as well as powdered bone or may be a synthetic HAp, apatite carbonate, or β-TCP etc. obtainable from a well-known method or a method known in public. Calcium phosphate of these kinds has no injurious character for a body.

As a setting solution, for example, a solution of an organic acid or a body-relating substance is used. As the body-relating substance, at least one kind of compound selected from a group of tannin, tannin derivatives, and body-relating organic acids is used. All of tannin, tannin derivatives, and said body-relating organic acids are substances relating to a body, so that they have no injurious character for a body.

As a tannin, for example, tannic acid is used. The tannin derivatives mean metal salts of tannic acid (for example, tannic acid zinc salt and tannic acid aluminum salt), tannic acid albumin, pyrogallol, and the like. As the tannin and tannin derivatives, any kind can be used. Hereinafter, although tannin is explained as an example, the tannin derivatives can be used in the same way. Tannin is, in comparison with hitherto known setting agents, very low in hardening rate and also, it is a setting agent, where working efficiency in the mixing and kneading does not almost decrease, that is, a hardening adjuster. Also, if tannin is used for a hardening material for dental use, a healing effect on inflammation in the oropharynx and pharynx mucous membrane can be expected due to a slow release of a constant concentration of tannin from the hardened product, and a preventive effect on a carious tooth can be expected due to prevention of dissolution of the tooth protein. The tannin concentration in a tannin solution is not especially limited, but when the slow release of a constant concentration of tannin is considered, a range of 0.1~70% (w/w) is preferred, a range of 0.1~30% (w/w) is preferred under a condition of coexistence with an organic acid, a range of 0.1~20% (w/w) is preferred under a condition of coexistence with collagen, and a range of 0.1~10% (w/w) is preferred under a condition of coexistence with an organic acid and collagen. If below these ranges, there is a case that a delay effect on hardening is not displayed and a case that slow release of a constant concentration of tannin from the hardened product cannot take place. If above these ranges, there is a case that the hardened product may collapse in an aqueous solution.

As the organic acid, there is used an acid of one kind alone or an acid mixture of two or more kinds, the acid selected from a group of organic acids relating to a living body such as, for example, citric acid, hydroxysuccinic acid, malonic acid, glyceric acid, and glutaric acid. These organic acids give a hardened product of hard quality by being mixed and kneaded with the calcium phosphate powder. The concentration of the organic acid in an organic solution is not especially defined, but a range of 0.1~90% (w/w) is preferred and, under a condition that tannin coexists, a range of 0.1~90% (w/w) is preferred and, under a condition that collagen coexists, a range of 0.1~70% (w/w) is preferred and, under a condition that tannin and collagen coexist, a range of 0.1~70% (w/w) is preferred. If below these ranges, after mixing and kneading, the hardened product becomes extremely low in physical strength and may sometimes collapse in an aqueous solution and, if above the ranges, crystals sometimes separate from the setting solution before mixing and kneading.

In the present invention, collagen and/or collagen derivatives (hereinafter simply referred to as "collagen") are used as a powder or in a melted state. This choice is properly carried out according to a procedure. In any case, when a powder component and a liquid component are mixed and kneaded, it is preferred for the collagen that it once dissolves and fibrillation takes place accompanied by hardening. If collagen has already converted into fibrils when it is mixed and kneaded, there may occur a problem that the fibrils separate.

In a case that collagen is used in a melted state, collagen can be used by dissolving it into said setting solution or it can be used by preparing a collagen solution other than a setting solution. When collagen is dissolved, an aqueous solution is prepared by dissolving it into water or into a setting solution of dilute concentration. In a case that collagen is used in a powder state, it may be used by mixing with said calcium phosphate powder or by separating from the calcium phosphate powder.

The proportion of collagen used is preferred to be 0.02~100 parts by weight against 100 parts by weight of the calcium phosphate powder. If the proportion of collagen used deviates from this range, there sometimes occurs a problem that a chemical bond on an interface between a coagulated, hardened product and a hard body tissue becomes weak or the mixing and kneading operation becomes difficult.

As collagen, there are used one kind or two kinds or more selected from collagen treated with alkali, collagen made soluble with neutral salts, collagen made soluble with an enzyme, and derivatives of these collagens.

A kind of collagen generally undergoes fibrillation within a very short time under physiological conditions (for example pH 7.0~7.4, temperature of 36°~37° C., salt concentration of 0.14M). Accordingly, if such kind of collagen is used as a hardening adjuster, collagen which has converted into fibrils coagulates and sometimes separates from a calcium phosphate-coagulated product. If this separation takes place, a complex derived from a chemical binding of HAp with collagen cannot be obtained. Thus, to obtain this complex, collagen which does not undergo fibrillation within a short time is preferred for use. However, if the collagen species have this character, they are not limited to the type I collagen and, the type II, III, and IV collagens also can be used. Said very short time means 8 minutes, or more preferably about 10 minutes.

As collagens which do not undergo fibrillation under the physiological conditions, there are, for example, decomposed gelatin (water-soluble gelatin or gelatin 21, products of Nitta Gelatin Inc.), type IV collagen (type IV collagen produced by Collagen Corporation), collagen made soluble with neutral salts (type I collagen), collagen treated with an alkali (type I collagen), succinated collagen (type I collagen), and methylated collagen (type I collagen). Also, as collagens which undergo fibrillation under the physiological conditions within 8 minutes, there are cited Cellmatrix type I-A produced by Nitta Gelatin Inc. and Cellgen I-AC produced by Kouken Co., Ltd. and so on. As collagens which undergo fibrillation with a time longer than 8 minutes, there are cited, for example, atterocollagen (type I collagen: Cellmatrix LA produced by Nitta Gelatin Inc., Cellgen produced from Kouken Co., Ltd., Vitrogen-100 produced from Collagen Corporation and so on.), collagen soluble in an enzyme (type I collagen: Cellmatrix type I-P produced from Nitta Gelatin Inc. and so on.), type II collagen (Cellmatrix Type II produced from Nitta Gelatin Inc. and so on.), type III collagen (Cellmatrix type III produced from Nitta Gelatin Inc. and so on), type IV collagen (Cellmatrix type IV produced from Nitta Gelatin Inc. and so on.). In this invention, these kinds of collagens can be used with proper selection.

In a case that collagen is used in this invention, not only fibrillation of collagen, but also coagulation and hardening of calcium phosphate proceed in parallel or almost in parallel, and a hardened product derived from coalescence of collagen fibrils and a calcium phosphate-hardened product into one body can be obtained. With these, the hardened product obtained makes a sufficient chemical bond with a hard body tissue.

As a collagen, atterocollagen is favored for use. Aterocollagen is, for example, collagen in which a part or a whole of a teropeptide at a terminal end of the molecule is removed by treatment with an enzyme and it has no injurious character for a body. Collagen may be used by dissolving it in a setting solution, as a solution independent of the setting solution, or in a powder state. Although the collagen concentration in a collagen solution is not especially limited, it is preferred to be in a range of 0.01 ~35% (w/w), under a condition of coexistence with an organic acid, preferred to be in a range of 0.05~35% (w/w) and, under a condition of coexistence with tannin, preferred to be in a range of 0.01~30% (w/w), and under a condition of coexistence with an organic acid and tannin, preferred to be in a range of 0.01~30% (w/w).

If below these ranges, a delaying effect on hardening by collagen and tannin may not be displayed. If above these ranges, collagen may decompose in a solution of an organic acid before mixing, or the viscosity of the solution may be elevated to too great an extent. In the case that collagen is used in a powder state, that having the forementioned average particle diameter is favored due to the above reason. As said collagen derivatives, are cited, for example, gelatin, decomposed gelatin (or polypeptide), succinated collagen, and methylated collagen.

In the present invention, the progress of the hardening reaction of calcium phosphate powder is adjusted by using at least one kind selected from a group of tannin, tannin derivatives, collagen, collagen derivatives, and organic acids. With this adjustment, operation efficiency for kneading is improved, the ratio of powder to liquid can be raised, and a hardened product of higher strength can be obtained. Also, in an application requiring a relatively long time for sealing, for example, as a root canal sealer for filling a cavity in a tooth root canal, it can be used. Besides, the delaying effect on hardening is greater in the combined use of both tannin and collagen than an use of each one alone.

The hardening adjuster relating to the present invention refers to the undermentioned types (I) and (II).

(I) A compound which, by combining it with at least either one of α-TCP and 4CP as well as water, undergoes hardening in a much longer time period (for example, one hour or more), as compared with a setting solution which has been previously used and composed of only an organic acid, and does not lower the operation efficiency for kneading.

(II) Rather than in the case that the hardening is carried out by using at least one of either α-TCP and 4CP, water, and one or more additional compounds, in the case that the hardening is further carried out by using one additional compound (that is, in total, two or more kinds of compounds), the time for hardening can be controlled without lowering the operation efficiency for kneading. In this case, said two or more kinds of compounds in the hardening adjuster of type (II) will be explained in more detail. When said additional one kind of compound is added, the compound which is replaced in a result may be α-TCP, 4CP, water, or other components which are able to constitute a hardening material. When said additional one kind of compound is replaced with any other component constituting a hardening material, the time for hardening can be controlled, after replacement more than before replacement, without lowering the operation efficiency for kneading. For example, when tannic acid is added to a system in which the powder 25 agent is 100% of α-TCP and the liquid agent is 35% of citric acid and 65% of water, if in any of the following methods (1)~(3), the time for hardening is delayed with addition of tannic acid, the citric acid and tannic acid are called a hardening adjuster.

(1) Five parts in the 100 parts of α-TCP are replaced with tannic acid.

(2) Five parts in the 65 parts of water are replaced with tannic acid.

(3) Five parts in the 35 parts of citric acid are replaced with tannic acid.

As shown in FIG. 5 (c), citric acid and malic acid are hardening adjusters in the case that citric acid and malic acid are in combined use. When the total concentration of the organic acids is constant (for instance, 45%), if proportion of malic acid to a sum of malic acid and citric acid is equal to 0.5 or more, the time for hardening becomes longer than in a case that citric acid alone is used. Also, in a solution of malic acid alone, if water is replaced with citric acid, the hardening time becomes longer than in the case that malic acid alone is used. Further, in a solution of citric acid alone, if water is replaced with malic acid, the hardening time becomes longer than the case that citric acid alone is used under a condition that concentration of citric acid is 9% or less. In FIG. 5 (c), the broken line shows congelation time in the case that malic acid in a 45% (a sum of citric acid and malic acid) solution is replaced with water and one point-dotted chain line shows congelation time in a case that citric acid in a 45% (a sum of citric acid and malic acid) solution is replaced with water.

As shown in FIG. 6, citric acid and malonic acid are hardening adjusters in a case that citric acid and malonic acid are in combined use. When the total concentration of the organic acids is constant (for instance, 45%), the congelation time becomes longer than in the case that citric acid alone is used. Also, if water is replaced with citric acid in a solution of malonic acid alone, or if water is replaced with malonic acid in a solution of citric acid alone, the congelation time becomes longer in both the cases. In FIG. 6, the broken line shows the congelation time in the case that malonic acid in a 45% (a sum of citric acid and malonic acid), solution is replaced with water, and the one point-dotted chain line shows the congelation time in a case that citric acid in a 45% (a sum of citric acid and malonic acid) solution is replaced with water.

In the case that said hardening adjuster provides hardening material, an essential reason is as follows.

When there is a hardening material comprises of α-TCP and/or 4CP, water, and one kind of organic acid (for example, an aqueous solution composed of 100% of α-TCP and an aqueous 45% solution of citric acid), two methods are considered as the ones to delay the hardening without the use of a hardening adjuster. The first one, as seen in FIG. 7 (c), is a method in which the concentration of a solution is raised (that is, due to replacement of water by an organic acid), but this method requires an increasing force for kneading as the concentration of the organic acid increases, so that there is a deficiency that it becomes very bad in efficiency of operation. The second one, as shown in each (c) of FIG. 8 through FIG. 12, is a method in which a ratio of powder to liquid is lowered (the liquid proportion is raised), that is, due to replacement of calcium phosphate powder with water and an organic acid, but this method shows decreasing strength as a ratio of powder to liquid becomes lower and thus, there is a weak point that the physical properties of the material becomes very low after hardening, for example, an increase of decomposition percentage. To delay the hardening by compensating for these weak points (lowering of operation efficiency during kneading and of physical properties after hardening), there is required the above-described hardening adjuster.

The powder agent and/or setting liquid in hardening materials in the present invention may be used in conjunction with, if necessary, any one or more selected from polysaccarides such as arginic acid, carrageenan, pectin, xanthane gum, locustbean gum, and jellan gum, which converts into a gel by a calcium ion, and mucopolysaccharide, chitin, and chitosan. Also, to add viscosity during operation and to thereby improve operation efficiency, an adhering agent for said powder agent and/or setting liquid such as polyalkylene glycol, polyethylene glycol, polyvinyl alcohol, polyvinylpyrrolidone, and dextran and so on may be added in a degree that they do not participate in the reaction or do not adversely affect the physical properties.

The hardening materials in this invention are able to undergo hardening by mixing and kneading at about room temperature or temperature of a living body and thus, there is no problem of cell death by generation of reaction heat.

The hardening materials in the present invention, for example, are as follows:

(1) A system composed of the combination of calcium phosphate powder and tannin.

As materials in this system, tannin is a hardening adjuster and used as a tannin solution. The hardened product is also a slow releasing material of tannin. Although the ratio of powder to liquid for materials in this system is not especially limited, a range of $0.1 \sim 5$ m/l is preferred. If below this range, the hardening may become insufficient, and if above the range, the kneading under room temperature may become insufficient.

A reaction mechanism for materials in system (1) is considered, for example, as follows on the basis of analysis data by X-ray powder diffraction, infrared absorption spectra, and scanning electron microscope. When calcium phosphate powder and a tannin solution is mixed and kneaded at room temperature or around living body temperature, octacalcium phosphate [$Ca_8H_2(PO_4)_6 \cdot 5 H_2O$: hereinafter referred to as "OCP"] is formed by coordination of water to 4CP in the powder. Also, in a case that $\alpha$-TCP is contained in the material by coordination of water with the $\alpha$-TCP, noncrystalline calcium phosphate [$Ca_3(PO_4)_2 \cdot n H_2O$: hereinafter referred to as "ACP"] is formed. On the other hand, tannin forms an associated material, which is considered as fibril-like. The OCP and ACP cohere with the tannin-associated material and, under this condition, the hardening progresses with conversion of OCP and ACP into HAp.

(2) A system composed of the combination of calcium phosphate powder, tannin, and collagen.

In the materials in this system, tannin and collagen are hardening adjusters. Also, tannin works on collagen for crosslinking. The hardened product from the materials in this system becomes a slow releasing material of tannin. Since collagen is contained in this system, affinity with a living body tissue in the neighborhood is excellent. Collagen may be used by preparing a solution independent of the tannin solution, by dissolving it in the tannin solution, or by using it in its powder state.

Although the proportion of the materials in this (2) system is not especially limited, a range of $0.01 \sim 20$ parts by weight of tannin and a range of $0.01 \sim 20$ parts by weight of collagen against the $10 \sim 80$ parts by weight of calcium phosphate powder are preferred. If tannin is below the range, there may be cases that the hardening becomes insufficient or the slow release of a constant concentration of tannin from the hardened product is impossible, and if above the range, the calcium phosphate powder is sometimes not sufficiently kneaded during the kneading operation. If collagen is below the range, the strength of the hardened product is sometimes too low, and if above the range, there may be a case that sufficient kneading is not possible.

A reaction mechanism of the (2) system is considered, for example, as follows on the basis of analysis results from X-ray powder diffraction, infrared absorption spectra, and scanning electron microscope and so on. When calcium phosphate powder, a tannin solution, and collagen are mixed and kneaded at room temperature or around living body temperature, OCP is formed with coordination of water to 4CP in the powder and, in a case that $\alpha$-TCP is contained, ACP is formed with coordination of water to the $\alpha$-TCP. On the other hand, a complex having a structure derived by crosslinking between collagen and tannin is formed. The hardening progresses by HAp, which is converted from OCP and ACP, crystallizing and cohering to the forementioned complex, which is considered as fibril-like.

When the materials in the (1) and (2) systems, each of which is mixed and kneaded as described above, the hardening progresses very slowly compared to the case that an organic acid is used as a hardening agent, and a hardened product of soft quality is obtained. For example, the hardening is complete within about $1 \sim 2$ days after initiation of kneading at room temperature or around living body temperature. Because of this, the materials in the (1) and (2) systems, for example, can be used as a root canal sealer for filing a cavity in root canal.

(3) A system composed of the combination of a calcium phosphate powder, an organic acid, and collagen.

In this system also, the organic acid and the collagen are hardening adjusters. Collagen may be used by preparing a solution independent of an organic acid solution, by dissolving the collagen into an organic acid solution, or used in a powder state.

Although the proportion of materials used in the (3) system in not especially limited, a range of $5 \sim 70$ parts by weight of an organic acid and a range of $0.1 \sim 30$ parts by weight of collagen against the $30 \sim 80$ parts by weight of calcium phosphate powder are preferred. If the organic acid is below the range, the hardening sometimes becomes insufficient, and if above the range, a delaying effect of collagen on the hardening is sometimes not displayed. If the collagen is below the range, the strength of the hardened product is sometimes not enhanced, and if above the range, kneading under room temperature is not sufficiently possible.

A reaction mechanism of materials in the (3) system is considered, on the basis of analysis results from X-ray powder diffraction, infrared absorption spectra, and scanning electron microscope, for example, as analogous to a collagen-calcified model of a living body hard tissue, and is as follows. When calcium phosphate powder, an organic acid, and collagen are mixed and kneaded at room temperature or around living body temperature, a chelate bond is formed between calcium atoms of 4CP and $\alpha$-TCP in the powder and the carboxyl groups in the organic acid and thus, a neutralization reaction progresses. On the other hand, collagen converts into fibrils and the chelated product coheres with the collagen fibrils. In the presence of water and at room temperature or around living body temperature, the chelated products existing on a surface of the hardened product and on a surface of the pores and the unreacted 4CP and $\alpha$-TCP form OCP and ACP by undergoing a hydration reaction, and then the OCP and ACP are converted into HAp which crystallizes into collagen fibrils, and thereby the hardening progresses.

(4) A system composed of the combination of a calcium phosphate powder, an organic acid, tannin, and collagen.

The materials in this system involve an organic acid, tannin, and collagen as hardening adjusters. The hardened product from the materials in this system becomes a slow releasing body of tannin. Each of tannin and collagen may be used by preparing a solution independent of an organic acid solution, by dissolving them in the organic acid solution, or by preparing a solution containing both tannin and collagen. Also, collagen may be used in a powder state.

Although the proportion of materials used in the (4) system is not especially limited, a range of 5~60 parts by weight of an organic acid, a range of 0.05~10 parts by weight of tannin and a range of 0.05~30 parts by weight of collagen against the 30~80 parts by weight of calcium phosphate powder are preferred. If the organic acid is below the range, the hardening sometimes becomes insufficient, and if above the range, unreacted organic acid sometimes is eluted in large quantity. If tannin is lower than the range, the strength of the hardened product becomes low and, in addition, a delaying effect on hardening is not sometimes displayed, and if above the range, there may be a case that kneading under room temperature becomes insufficient. If the collagen is below the range, the strength of the hardened product becomes low and a delaying effect on hardening is not displayed. If it is above the range, there is a case that kneading under room temperature becomes insufficient.

A reaction mechanism of the materials in the (4) system is considered, on the basis of analysis results from X-ray powder diffraction, infrared absorption spectra, and scanning electron microscope, for example, as analogous to a collagen-calcified model for a bone tissue, and is as follows. When calcium phosphate powder, an organic acid solution, tannin, and collagen are mixed and kneaded under room temperature or around living body temperature, a chelate bond is formed between calcium atoms of 4CP and α-TCP in the powder and the carboxyl groups of the organic acid and thus, a neutralization reaction progresses. On the other hand, a complex (which is considered as fibril-like) constructed by crosslinking of tannin with collagen is formed.

The chelated compound coheres to the complex. In the presence of water and at room temperature or around living body temperature, the chelated compound existing on a surface of the hardened product and on a surface of the pores and the unreacted 4CP and α-TCP form OCP and ACP by undergoing a hydration reaction and, the OCP and ACP converts into HAp which crystallizes with aid complex, and thus the hardening progresses.

(5) A system composed of the combination of calcium phosphate powder, an organic acid, and tannin.

In this system, the organic acid and tannin are hardening adjusters. The hardened product from materials in this system is a slow releasing body of tannin. Tannin may be used by preparing a solution independent of the organic acid solution or by dissolving it in the organic acid solution.

Although the proportion for use of materials in the (5) system is not especially limited, a range of 5~60 parts by weight of the organic acid and a range of 0.01~10 parts by weight of tannin against the 30~80 parts by weight of the powder are preferred. If the organic acid is below the range, the hardening may become insufficient, and if above the range, it is sometimes impossible to knead sufficiently under room temperature. If tannin is below the range, a delaying effect on hardening is sometimes not displayed and a slow release of constant concentration of tannin from the hardened product may not be possible. If above the range, it is sometimes impossible to knead sufficiently under room temperature.

A reaction mechanism of the (5) system may be considered, one the basis of analysis results from X-ray power diffraction, infrared absorption spectra, and scanning electron microscope, for example, as follows. When calcium phosphate powder, an organic acid solution, and tannin are mixed and kneaded under room temperature or around living body temperature, a chelate bond is formed between the calcium atoms of 4CP and α-TCP in the powder and the carboxyl groups of the organic acid and thus, a neutralization reaction progresses. On the other hand, tannin forms an association compound (which is considered as fibril-like), with which the chelated product coheres. In the presence of water and at room temperature or around living body temperature, the chelated product and the unreacted 4CP and α-TCP form OCP and ACP by undergoing a hydration reaction and, the OCP and ACP converts into HAp which crystallizes with the tannin association compound, and thus the hardening progresses.

(6) A system composed of the combination of calcium phosphate powder and two or more kinds of organic acids.

In this system, the two kinds or more of organic acids are hardening adjusters. The two or more kinds of organic acids may be used by dissolving them into the same solution or into separate solutions. The composition ratio of the two or more kinds of organic acids is variable with the combination of the organic acids. For example, as mentioned above, it is just as explained with reference to FIG. 5 (c) and FIG. 6.

The hardening materials in said (5) and (6) systems undergo mixing and kneading of the powder component and the liquid component at the desired temperature, for example, room temperature, to convert these components into a slurry or a paste, which are then applied, injected, or plugged up for a treatment part. The slurry and paste undergo a chemical reaction under in vivo environments and thereby, a chelate bond is formed between the calcium atom in a α-TCP and the carboxyl group in an organic acid by undergoing a neutralization reaction and thus, the hardening progresses.

In the presence of water and at room temperature or around living body temperature, the chelated products existing on a surface of the hardened product and on a surface of the pores and the unreacted α-TCP yield ACP by undergoing a hydration reaction, where ACP transforms into HAp. The forming hardened product shows a structure similar to a hard tissue of the living body and combines with the hard tissue of the living body. In the case where tannin is used for the hardening material composition, the hardened product is a slow releasing body of tannin.

The hardening materials in said (5) and (6) systems can be used as a sealing material and an adhesive etc. for the hard tissue of a living body, for examples, a treatment material for periodontosis, a sealing material for root canals, a sealing material for broken bones, and an adhesive for the hard tissue.

When the materials in said (3)~(5) systems are mixed and kneaded, the progress of the hardening becomes slower than a case of where tannin or collagen is not used. For example, at room temperature or around living body temperature, the hardening is completed during 5~60 minutes after initiation of the kneading and a hardened product of hard quality is obtained. Because of this, the ratio of calcium phosphate powder to an organic acid can be raised, so that strength of the hardened product can be increased. In particular, if collagen is used, without a raise of the ratio of calcium phosphate powder to an organic acid the compression strength increases and, in addition, after said hardening is completed, the compression strength increases with time passage and elasticity is enhanced. The materials in said (3)~(5) systems can be used as sealing, bonding, or dental prosthesis materials for the hard tissues of a living body, for example, as bone cement and cement for dental use and so on.

When a hardened product at an initial stage obtained from mixing and kneading of the materials in said (3)~(4) systems is immersed in a physiological PBS (phosphate-buffered saline) at 37° C., the resisting force for crushing increases with the passage of time. That is, when the materials in said (4) and (5) systems are used as bone cement, the strength increases with the passage of time even after they are buried. This is considered due to the use of collagen.

When the materials in said (3)~(6) systems are converted into bone cement and then buried in the bone of a living body, since the cement is active for the living body and thus, it takes a bone-like structure and coalesces into one body with the bone tissue. In the case that α-TCP is used, since α-TCP is biodegradable, it can be gradually substituted by a new bone during a period from 6 months to 1 year. That is, in the hardening materials relating to the present invention, when a material in which an organic acid is used as a setting agent and at least either one of tannin and collagen is used as a hardening adjuster is used as a bone cement, the material is, after being buried, substituted by bone tissue with the passage of time and thus coalesces into one body with an already existing part.

Besides, all the materials in said (1)~(6) systems are possible to contain any material other than the above-described materials as far as the purpose attainment in the present invention is not altered.

Also, the use is not limited within said examples.

All the materials in said (1)~(6) systems, because a setting agent is used therein, can control the length of time for hardening without lowering operation efficiency for kneading. Incidentally, in the case that the hardening materials in this invention are for bone cement or dental cement and so on, it is preferred to use such component composition as the undermentioned (i)~(iv). This is, as mentioned later, because strength and disintegration of the hardened product as well as time for hardening is within a range suitable for practical use. Among the undermentioned (i)~(iv) hardening materials, materials (i) and (ii) are included in the materials of said (5) system and materials (iii) and (iv) are included in the materials of said (6) system.

(i) A hardening material in which α-TCP, an organic acid, and water are essential components, in composition proportion of said water, the organic acid, and tannin acid, the total of the organic acid and tannin acid is 40~48% by weight (hereinafter referred to as simply "%"), and the residual part is water, said organic acid is citric acid and/or malonic acid, and the mutual proportion of citric acid, malonic acid, and tannic acid is 60~90 parts by weight for citric acid (hereinafter referred to as simply "part" for part by weight), 0~35 parts or less for malonic acid, and 30 parts or less for tannic acid against the total of 100 parts of these three acids, but when the malonic acid is 0 part, citric acid is 70~89 parts and tannic acid 30~11 parts.

(ii) A hardening material in which α-TCP, an organic acid, and water are essential components, in composition proportion of said water, the organic acid, and tannic acid, the total of the organic acid and tannic acid is 40~48% and the residual part is water, said organic acid is citric acid and/or malic acid, and the mutual proportion of citric acid, malic acid, and tannic acid are, respectively, 0~65 parts, 20~90, and 15 or less against 100 parts of the total of the three components.

(iii) A hardening material in which α-TCP, organic acids, and water are essential components, in composition proportion of said water and the organic acids, the organic acids are 40~48% and the residual part is water, said organic acids are citric acid and malonic acid, the mutual proportion of these organic acids is 65~90 parts for citric acid and malonic acid, the mutual proportion of these organic acids is 65~90 parts for citric acid and 10~35 for malonic acid against 100 parts of the total organic acids.

(iv) A hardening material in which α-TCP, organic acids, and water are essential components, in composition proportion of said water and the organic acids, the organic acids are 40~48% and the residual part is water, said organic acids are citric acid and malic acid, and the mutual proportion of these organic acids is 10~65 parts for citric acid and 35~90 for malic acid against 100 parts of the total organic acids.

In said composition proportion of water and an organic acid, if the composition proportion of the organic acid is less than 40% against the total weight amount of both the materials, the hardening becomes so rapid during mixing, the handling becomes difficult, and if the proportion exceeds 48%, the decomposition percentage may become high, the viscosity may become so high that the kneading becomes difficult, or may result in elution of the unreacted acid which gives an impetus for a living body and causes an inflammatory reaction.

If the mutual proportion for combined use of said organic acids is deviated from said corresponding range, effects due to the combined use cannot be obtained.

Hereinafter, the process where the present inventors found the forementioned means for a solution is explained in detail.

The present inventors, to solve said objects, studied the reason why practical use is not carried out and, as a result, found that the hitherto known hardening materials are not satisfactory for all the undermentioned (1)~(3) capacities and are defective in any of the capacities.

(1) Strength of the hardened product is high.

(2) Under physiological conditions, stability of the hardened product is high and decomposition character is low.

(3) During mixing and kneading, the hardening process proceeds with proper slowness and the efficiency for operation is superior.

The inventors, to satisfactorily achieve all of these (1)~(3) capacities and to obtain superior affinity for the living body hard tissue, carried out studies with a consideration that, rather than using a calcium phosphate besides α-TCP and an addition of a component other than the organic acid to a setting solution, a superior idea is to use an organic acid which is known, according to previous research, to have no character injurious to a body and to set it most suitable concentration range.

As organic acids for the hardening materials which are of high possibility for use are known monocarboxylic acids, dicarboxylic acids, and tricarboxylic acids. In particular, the dicarboxylic acids and the tricarboxylic acids in the Krebs cycle are superior complex-forming reagents for calcium and a high possibility for their use is expected. For almost all the monocarboxylic acids and for the dicarboxylic acids, since the chelate-forming force is weak, the decomposition percentage often rises extremely after the hardening is finished (for example, pyruvic acid, glyceric acid, and lactic acid, and also, as a dicarboxylic acid, maleic acid). Also, due to weak chelate-forming force, some acids show a long hardening time (for example, the cases of lactic acid and glucuronic acid). Due to the weak chelate-forming force, there are acids with which a calcium salt are formed within a short time and, as a result, the hardening time becomes extremely short (for example, as a monocarboxylic acid, pyruvic acid and, as a dicarboxylic acid, tartaric acid, oxalic acid, and glycolic acid). Although the tricarboxylic acids have relatively strong chelate-forming force and are expected to very often show superior physical properties after the hardening (in strength and decomposition percentage etc.), the majority show poor solubility in water and are hard to obtain in suitable concentration (for example, aconitic acid, oxaloacetic acid, and oxalosuccinic acid, etc.). Also, among the dicarboxylic acids, some acids show poor solubility (for example, succinic acid and fumaric acid etc.). From consideration of these, the acids of high solubility in water from the group of the di- or tricarboxylic acids can be expected to be of practical use. Also, in a group of tannin, since tannic acid shows weak chelate-forming force, its hardening time becomes long, but it was listed for examination because it works as a setting agent as described above.

Accordingly, when the acids of no character which is injurious for a body in a great number of organic acids estimated to be usable as a hardening material, that is, all the organic acids shown in Table 1 (tannic acid is included in the organic acids mentioned here), are each used in a form of an independent aqueous solution as a setting solution were examined whether or not a concentration range which is satisfactory for the above-described (1)~(3) capacities can be set. At first, the solubilities of the organic acids for water were examined and, as a result, high solubility was shown with circle and poor solubility with cross in Table 1. The acids of poor solubility were excluded from the examination list and the acids of high solubility were further examined. The variation of resisting force for crushing (kg f/cm$^2$) when the citric acid concentration is varied is shown in FIG. 7 (a), the variation of decomposition percentage (%) with the above variation is shown in FIG. 7 (b), and the variation of coagulating time (min.) with the above is shown in FIG. 7 (c). On the basis of these graphs, said concentration range was examined. Other organic acids were also similarly examined.

TABLE 1

| Kind of organic acid | Solubility in water | Strength for crushing | Decomposition percentage | Coagulating time | Presence of concentration to satisfy three capacities at the same time |
|---|---|---|---|---|---|
| Citric acid | o | o | o | Δ | x |
| Formic acid | o | Δ | x | x | x |
| Acetic acid | o | x | x | x | x |
| Oxalic acid | o | Δ | Δ | x | x |
| Lactic acid | o | Δ | x | x | x |
| Tannic acid | o | Δ | — | x | x |
| Glycolic acid | o | o | Δ | x | x |
| Maleic acid | o | x | x | Δ | x |
| Itaconic acid | o | Δ | x | x | x |
| Fumaric acid | x | — | — | — | — |
| Polyglutamic acid | x | — | — | — | — |
| Polyasparaginic acid | x | — | — | — | — |
| Malic acid | o | o | Δ | o | x |
| Pantothenic acid | o | x | x | x | x |
| Tartaric acid | o | Δ | x | x | x |
| Glutamic acid | x | — | — | — | — |
| Phytic acid | o | Δ | Δ | x | x |
| Pyruvic acid | o | o | x | Δ | x |
| Malonic acid | o | o | Δ | o | x |
| Aconitic acid | x | — | — | — | — |
| Gluconic acid | o | x | x | x | x |
| Glyceric acid | o | x | x | x | x |
| Succinic acid | x | — | — | — | — |
| Oxaloacetic acid | x | — | — | — | — |
| Oxalosuccinic acid | x | — | — | — | — |
| Glucuronic acid | o | Δ | Δ | x | x |

In Table 1, the strength for crushing corresponds to said (1) capacity, the decomposition percentage to said (2) capacity, and the coagulating time to said (3) capacity, respectively. These capacities were examined on a basis of JIS T6602 under the conditions that the ratio between powder and liquid was 2.5 and the mixing and kneading were performed with hand-working. The results are presented for each of the capacities by showing with circles, if they are of a practical standard, with crosses if they are definitely are of an unpractical standard, with triangles if they are of a standard somewhat inferior than the practical standard, and also, by showing with circles if a concentration range where the three capacities are satisfied in the practical standard at the same time is held, and with crosses if it is not held.

As seen in Table 1, all the organic acids so far proposed do not have a concentration to satisfy all of said three capacities. However, citric acid, malic acid, and malonic acid are in outline satisfactory for said (1)~(3) (that is, capacities of the "cross" mark standard are absent), but it is understood that the other organic acids have a problem in any of the capacities (that is, those of the "cross" mark standard exist). Also, it is understood that the organic acids differ in effects on said (1)~(3) capacities depending upon their kinds. This difference is considered as arising from decalcification ability, rate of chelate-forming reaction and binding force with $Ca^{2+}$, and molecular weight of the organic acids, pH and stability with $Ca^{2+}$, and molecular weight of the organic acids, pH and stability with $Ca^{2+}$ of the mixed and kneaded products, and difference of varying percentage in the hardening density.

On the other hand, if the concentration of an organic acid in a setting solution is high, the resisting force for crushing becomes high, the coagulating time tends to be long, the decomposition percentage tends to be high, a considerable amount of force may be needed for the kneading operation, and sealing of a small gap in a living body may become difficult. Furthermore, if the concentration of an acid is high, the acid which did not react may undergo elution, and it gives an impetus to a living body and may cause an inflammatory reaction. On the contrary, if the concentration of an organic acid is low, there is a case that the hardening takes place at a time very soon after mixing, and there is a trend that the use becomes difficult. From consideration of these things, it is hoped that the concentration of the organic acid is about 35~50%.

Next, the inventors considered to satisfy said (1)~(3) capacities not by the use of an organic acid alone, but by the use of two kinds or more of organic acids in combination.

This is due to the fact that it was considered that there may be an organic acid which, even if its use alone is practically useless, shows a possibility of practical use if it is used in combination with an other acid. For example, as mentioned above, when only one acid is used, at least 30% or more of solubility in water is needed, but even if the organic acid is a tricarboxylic acid or a dicarboxylic acid which is itself of poor solubility, the acid is of sufficiently practical use as one important component when the kind of an acid used in combination is properly chosen and when solubility of the acid itself is 10% or more. Also, even if it is an organic acid or weak chelate-bonding force whose only one use is practically impossible, it can be used as one of main components in the case where an organic acid which is used in combination at the same time has a strong chelate-forming force.

Accordingly, by adjusting the total concentration of organic acids at 35~50% and by changing the proportion of the two kinds of organic acids, whether said (1)~(3) capacities can be all satisfied or not were examined. By using the especially superior three kinds of organic acids (citric acid, malic acid and malonic acid) selected from said 20 kinds or more of organic acids and by using each of those in combination with another organic acid, it was examined whether the capacity which was displayed in a case of only one acid used has been lost and also, whether the capacity which was not displayed in a case of only one acid used was revealed. These examinations were carried out as follows.

First, by using two kinds of organic acids in combination, an operation to exclude the organic acids which make worse the capacity in the case of only one acid used was carried out. The examinations were carried out according to the above procedure wherein the respective proportions of the organic acids were 90% for citric acid, malic acid, and malonic acid, the other organic acids were the remaining 10%, and the total concentrations of the organic acids was 45%. As a result, it was seen that, when the seven kinds of acids such as tannic acid, phytic acid, maleic acid, pyruvic acid, tartaric acid, oxalic acid, and glycolic acid were used in combination with each of citric acid, malic acid, and malonic acid, they did not make worse the capacity which was displayed in a case of the use of only one acid such as citric acid, malic acid, and malonic acid, and also that citric acid, malic acid, and malonic acid did not make worse the capacity which was displayed in a case of the use of only one acid.

Accordingly, by using in combination a set of two acids selected from the ten kinds of organic acids of citric acid, malic acid, malonic acid, tannic acid, phytic acid, maleic acid, pyruvic acid, tartaric acid, oxalic acid, and glycolic acid, was examined as to whether the proportion for use (ratio by weight) which increases all said three capacities exists or not. The examinations were carried out according to the above procedure by setting the total concentration of organic acids at 35, 40, 45, and 50%, respectively. FIG. 5 (a) shows resisting force for crushing in a case where malic acid and citric acid are used in combination and the total concentration is adjusted to be 45%. FIG. 5 (b) shows decomposition percentages in those cases. FIG. 5 (c) shows coagulating time in those cases. In these combinations, when the proportion of citric acid and malic acid was in a range from 10% vs 90% to 50 vs. 50, said (1)~(3) capacities were improved in the same degree or more, compared to cases where only one use of the respective acids was used. Similarly, in other combinations which were examined, the proportion for use wherein said (1)~(3) capacities were improved in the same degree or more was observed, compared to cases where only one of the respective acids was used.

From these results, there is seen no proportion for use which satisfies all the three capacities by using phytic acid, maleic acid, pyruvic acid, tartaric acid, oxalic acid and glycolic acid. However, if two kinds of acids optionally selected from citric acid, malic acid, malonic acid, and tannic acid are used, there is a proportion for use which satisfies all the capacities as seen in Table 2.

Next, from said four kinds of organic acids, three kinds were optionally selected and, on a basis of the numeral values in Table 2, were examined for the proportion of the organic acids which is satisfactorily for all said three capacities as carried out above. FIG. 4 is a diagram for a three component system of citric acid, malic acid, and tannic acid (the total concentration of organic acids is 35%). For the other three component systems, similarly prepared figures were also examined. Then, when said three capacities were examined outside the area C surrounded by the line which connects the numeral values of proportion for use in the two components system, it was found that capacity improvement was not achieved as the deviation from the area C increases. From these results, in the case where the three kinds of organic acids are used in combination, it was considered that the proportion which is the best to improve said three capacities can be found in an area obtainable from Table 2.

spective capacities were examined by setting the total concentration of organic acids at 35, 40, 45, 50%, it was

TABLE 2

| | Total concentration of organic acid in setting solution (weight %) | 35 | 40 | 45 | 50 |
|---|---|---|---|---|---|
| Proportion for use of two kinds of organic acids (%)*1 | citric acid / malic acid | $\frac{50}{50} \sim \frac{30}{70}$ | $\frac{70}{30} \sim \frac{20}{80}$ *2 | $\frac{50}{50} \sim \frac{10}{90}$ *2 | $\frac{40}{60} \sim \frac{20}{80}$ |
| | citric acid / malonic acid | $\frac{95}{5} \sim \frac{70}{30}$ | $\frac{95}{5} \sim \frac{65}{35}$ *2 | $\frac{90}{10} \sim \frac{60}{40}$ *2 | $\frac{90}{10} \sim \frac{80}{20}$ *2 |
| | citric acid / tannic acid | $\frac{90}{10} \sim \frac{70}{30}$ *2 | $\frac{95}{5} \sim \frac{70}{30}$ *2 | $\frac{95}{5} \sim \frac{70}{30}$ *2 | $\frac{95}{5} \sim \frac{85}{15}$ |
| | malic acid / malonic acid | none | $\frac{90}{10} \sim \frac{70}{30}$ *2 | $\frac{90}{10} \sim \frac{50}{50}$ | none |
| | malic acid / tannic acid | $\frac{90}{10} \sim \frac{70}{30}$ | $\frac{90}{10} \sim \frac{70}{30}$ | $\frac{90}{10} \sim \frac{80}{20}$ *2 | $\frac{90}{10} \sim \frac{85}{15}$ |
| | malonic acid / tannic acid | none | $\frac{80}{20} \sim \frac{95}{5}$ | $\frac{90}{10}$ | none |

*1 proportion for use in a case that, compared to the case of only one acid use, various properties were improved.
*2 those that the results of various properties were especially good.

On the other hand, the proportion for use wherein said three capacities are especially good is considered, from Table 2, to be in a range of where the total concentration of organic acids is set at 42.5% and, in both the proportions for use of 40% and 45% in Table 2, said three capacities were examined according to the following standards.

(A) A proportion for use in which the resisting force for crushing exceeds 110 kg f/cm². This numerical value is the general value which is realized with a hardening material available in a market at present.

(B) A proportion for use in which the decomposition percentage does not exceed 2%. This numerical value was set to prevent elution of an unreacted acid into a living body which may give an impetus and also, to prevent decomposition of hardened products in saliva or body fluids as well as deterioration of its strength within a short time.

(C) A proportion for use in which the coagulation time is in a range of 2.5~8.0 minutes. This numerical value range is derived from an operation characteristic when a user carries out the mixing and kneading of a hardening material.

With respect to the three component systems of citric acid, malonic acid and tannic acid, the area D which is satisfactory for said capacity (A) is shown by FIG. 3 (a), the area E which is satisfactory for said capacity (B) by FIG. 3 (b), and the area F which is satisfactory for said capacity (C) by FIG. 3 (c), respectively. In FIGS. 3 (a)-(c), the area G shows a proportion for use derivable from Table 2. By being performed similarly in the three component systems of citric acid, malic acid and tannic acid, in the three component systems of malic acid, malonic acid, and tannic acid, and in the three component system of citric acid, malic acid, and malonic acid, a proportion for use which is satisfactory for all said capacities (A)~(C) is shown in FIG. 1 and FIG. 2. That is, as seen in FIG. 1, in the three component system of citric acid, malonic acid, and tannic acid and, as seen in FIG. 2, in the three component system of citric acid, malic acid, and tannic acid, it is understood that all said capacities (A)~(C) are satisfied in only the two systems.

Furthermore, on the optional points in each of the areas A and B shown in FIG. 1 and FIG. 2, when reseen that the strength and the coagulation time in the case of 35% are inferior to those in the case of 40%, the composition percentage in the case of 50% is inferior to that in the case of 45%, and that all said three capacities are superior in the area of 40~48%.

As a result of the forementioned, as seen respectively in FIG. 1 and FIG. 2, said means for resolution in the very limited range was attained.

The hardening materials by setting as above the proportion for combination of water and an organic acid (or water, an organic acid, and tannic acid) and by setting the kinds of organic acids and the proportion for combined use of an organic acid and tannic acid as described above, are able to compensate one another for the physical properties which are inferior in the case of the use of only one of each organic acid. As a result, the strength of hardened products has become low, and further the coagulation time has become properly slow. In addition, in the case that tannic acid is used, slow release of tannic acid, which as a pain-killing effect, from a hardened product is possible.

In the hardening materials relating to the invention, 5% at maximum or less of a total amount of the organic acids can be replaced with an organic acid besides said four kinds of organic acids which are shown in Table 1 or an organic acid not shown in Table 1, or may be replaced with a salt derived from those acids as a component of a very small amount in a degree which does not damage the effects of this invention.

Also, an inorganic acid such as pyrophosphoric acid which participates in the reaction with a small amount, a salt of an inorganic acid, and a polymer material such as acrylic acid, polyacrylic acid, and alginic acid can be added up to 1% of the solution in case that an organic acid with water is mixed. Also, even if it does not directly participate in reaction, a protein substance such as collagen and collagen derivatives, a vitamin, and a polysuccaride, in a degree that an adverse effect on the physical properties is not given, can be added up to 2% of the solution in case that an organic acid with water is mixed.

The combination proportion of calcium phosphate to a setting solution, which is prepared by dissolving an organic acid in water, is preferably set by adjusting the ratio by weight of calcium phosphate to a setting solution (g/ml) (so-called ratio of powder to liquid) in a range of 1.0~3.3. If the proportion deviates from this range, there sometimes occurs a problem that the coagulation and hardening does not take place or the mixing and kneading and the sealing operation become difficult.

Furthermore, even if the ratio of powder to liquid is varied in a considerably wide range, the advantage that said (1)~(3) capacities do not widely vary can be obtained. Especially, in a three component system containing tannic acid and in a practically useful range of powder to liquid (the ratio of powder to liquid is 1.5~2.7), said three capacities are more stable than those in a two component system. In the typical case where a hardening material is usually used, because the powder is measured by a spoon without precise weighing and the liquid is measured by drop number, the ratio of powder to liquid is often and considerably scattered, the forementioned is a significant advantage. Also, since a three component system containing tannic acid is a system in which tannic acid slowly is released, a pharmacological effect such as astriction of an inflammatory trouble in the oropharynx mucous membrane can be expected.

For hardening materials relating to the present invention, as mentioned above, a main material is calcium powder in which at least either one of 4CP and α-TCP is an essential component and any of the undermentioned (a)~(f) is used as a hardening adjuster, so that the hardening proceeds at room temperature or around living body temperature and the hardening time can be increased with almost any absence of decrease in the operational efficiency for mixing and kneading and also, a character injurious to a body is absent. The hardening adjuster may be:

(a) At least one compound from among tannin and tannin derivatives.

(b) At least one compound from among tannin and tannin derivatives and at least one compound from among collagen and collagen derivatives.

(c) At least one compound from among collagen and collagen derivatives and one or more organic acids.

(d) At least one compound from among tannin and tannin derivatives, at least one compound from among collagen and collagen derivatives, and one or more organic acids.

(e) At least one compound from among tannin and tannin derivatives and one or more organic acids.

(f) Two or more organic acids.

Therefore, the hardening materials relating to the present invention can be utilized for an application wherein the hardening needs a long period of time, and for an application wherein a hardened product of high strength is needed by raising the ratio of calcium phosphate powder to a setting agent.

Since the hardening materials are the ones wherein a hardening adjuster of specially-defined composition is used as mentioned above, they have almost no characteristic which is injurious to a body, form a hardened product similar to the hard tissue of a living body, and have special properties to combine with the hard tissue of a living body and, therefore, the strength, decomposition percentage, and coagulating time of the hardened product are of practical use.

The hardening materials of this invention are not limited to the ones which contain only the essential components mentioned above, and other materials may be combined in an extent which does not disturb resolution of the objects of this invention. Also, among the hardening materials in this invention, said (i)~(iv) hardening materials may be, in addition to the above, combined with the other components in an extent which does not adversely affect upon said (A)~(C) capacities. Here, the other materials means, for example, water, calcium phosphate other than α-TCP (4CP, HAp, and OCP, etc.), X-ray contrast agents ($BaSO_4$ and bismuth salts etc.), pigments ($TiO_2$ etc.), coloring materials (β-carotene etc.), other kinds of inorganic oxides and inorganic salts (MgO, $MgCO_3$, and $Al_2O_3$ etc.), calcium gelation agents (jellan gum and chitosan etc.), coaking agents (polyalkylene glycol and polyvinyl alcohol etc.), inorganic acids (pyrophosphonic acid, orthophosphonic acid, polyphosphonic acid, and hydrochloric acid etc.), polymolecular materials (acrylic acid and polyacrylic acid etc.), organic acid salts (sodium citrate and calcium citrate etc.), employed alone or in combination of two or more kinds.

BRIEF DESCRIPTION OF THE DRAWINGS

FIG. 3 shows triangular coordinates representing the proportion of organic acids wherein.

Figure 1:
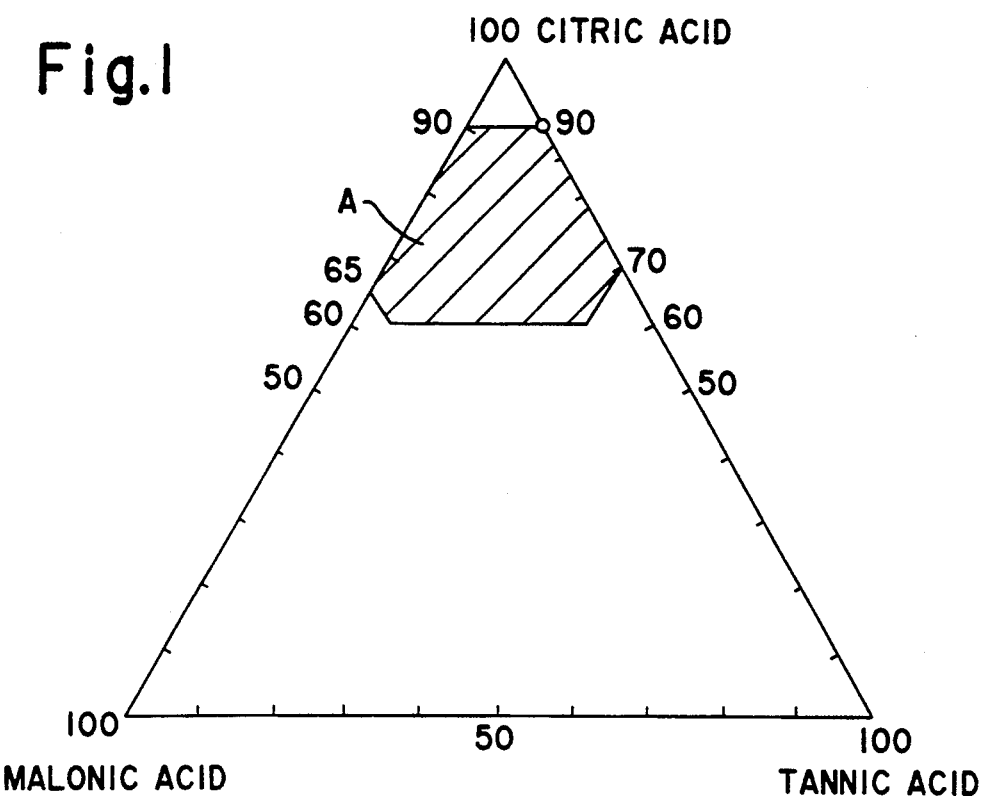
FIG. 1 shows triangular coordinates representing the proportion of organic acids which are hardening materials relating to the inventions in claims 9 and 13.
Figure 2:
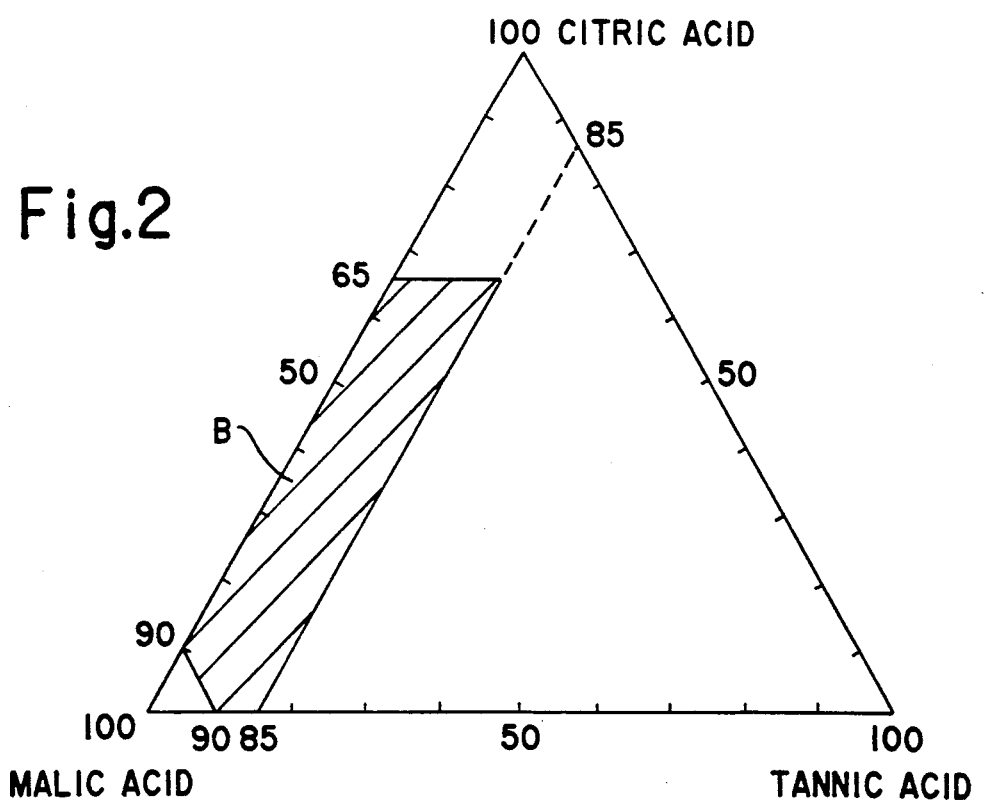
FIG. 2 shows triangular coordinates representing the proportion of organic acids which are hardening materials relating to the inventions in claims 10 and 11.
Figure 3A:
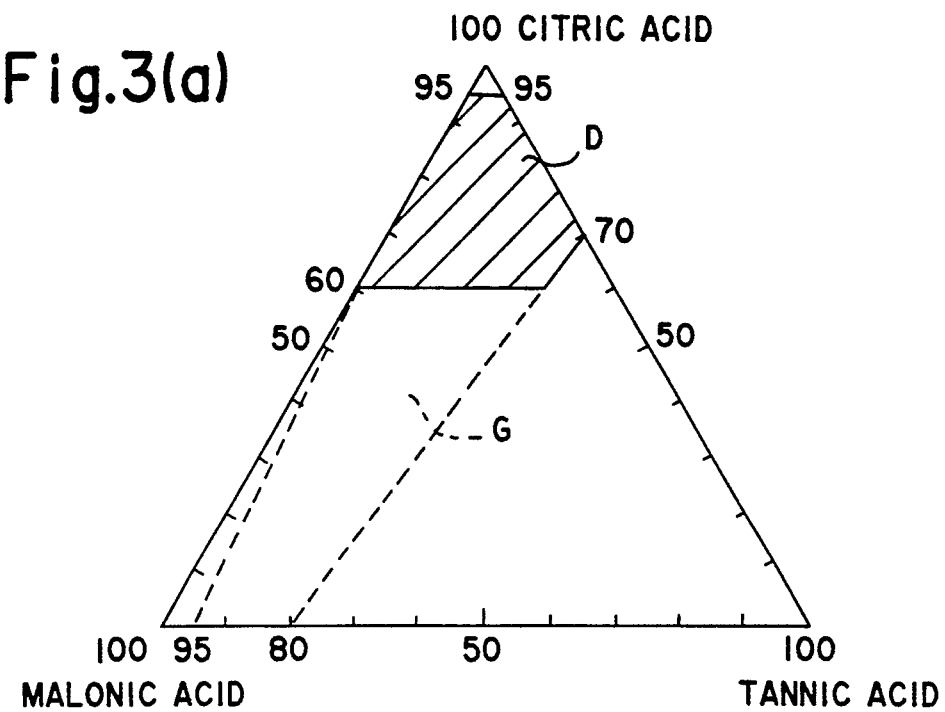
FIG. 3(a) shows resisting force for crushing
Figure 3B:
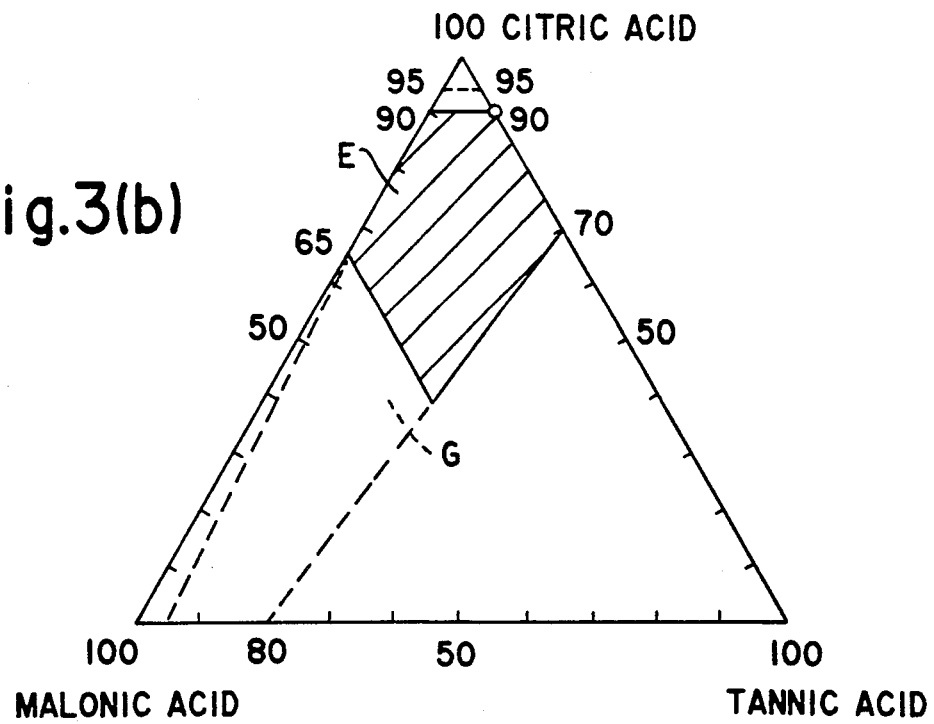
FIG. 3(b) shows decomposition percentage.
Figure 3C:
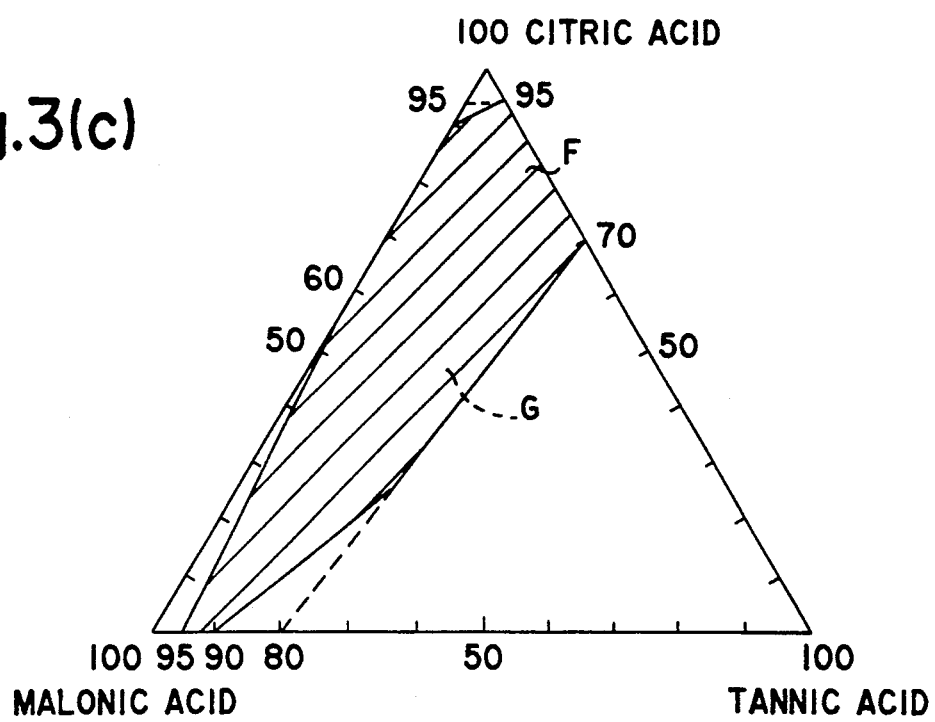
FIG. 3(c) shows coagulation time.
Figure 4:
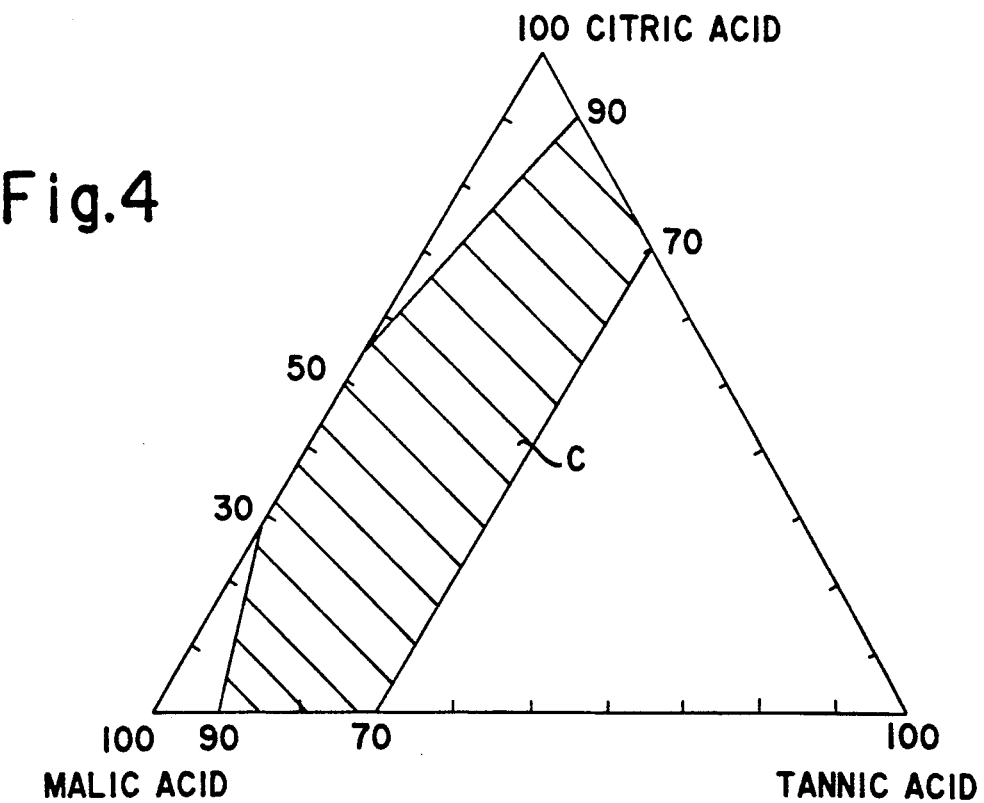
FIG. 4 shows triangular coordinates representing the proportion of three kinds of organic acids which were prepared on a basis of the, data in Table 2.
Figure 5A:
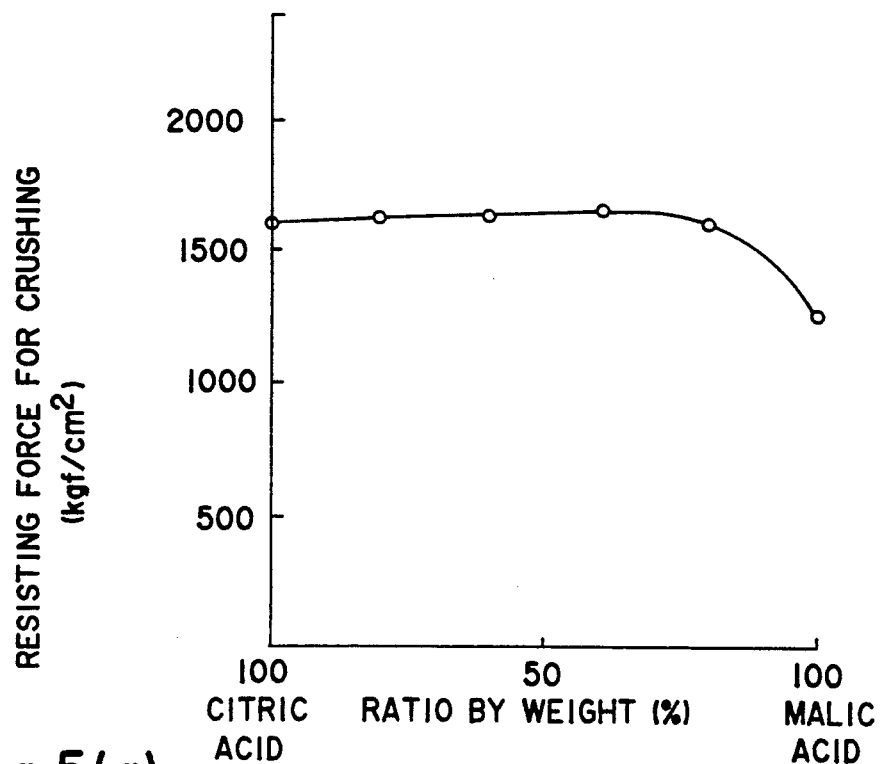
FIG. 5 shows the proportion in a case where two kinds of organic acids were used in combination wherein, FIG. 5 (a) is shows resisting force for crushing, FIG. 5 (b) shows decomposition percentage, and FIG. 5 (c) shows coagulating time.
Figure 5B:
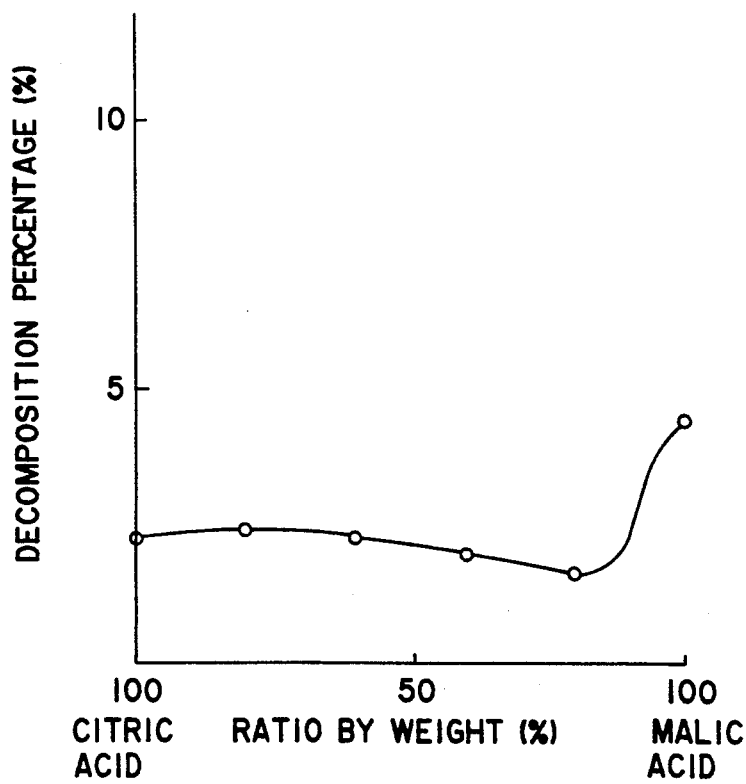
Figure 5C:
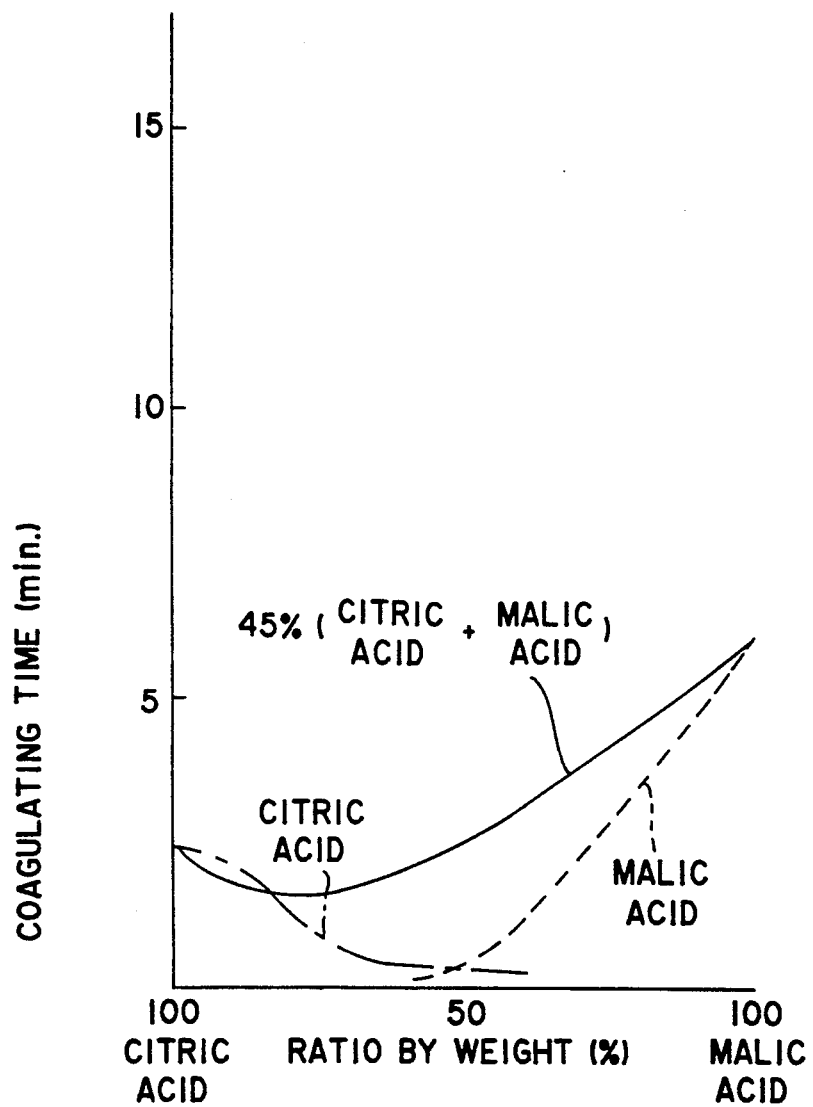
Figure 6:
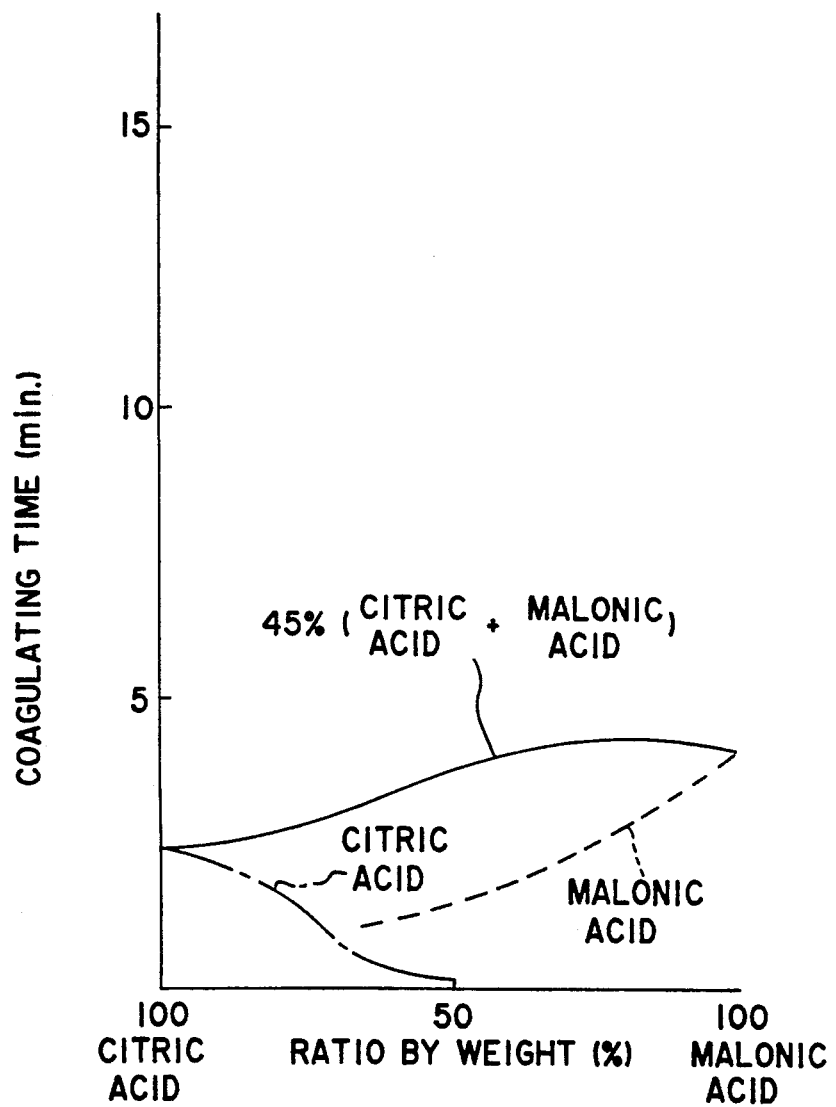
FIG. 6 is a graph showing a relationship between the proportion for use, when two kinds of organic acids are used in combination, and the coagulating time.
Figure 7A:
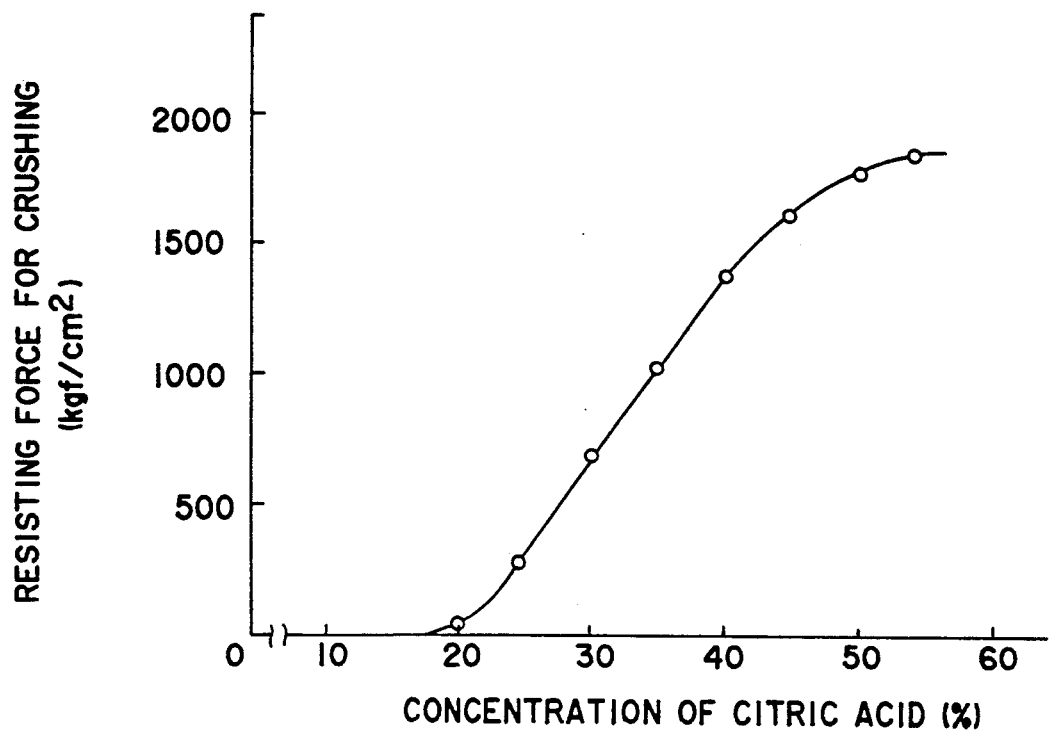
FIG. 7 shows the concentration when an organic acid is used alone and FIG. 7 (a) showing resisting force for crushing, FIG. 7(b) showing decomposition percentage, and FIG. 7(c) showing coagulating time.
Figure 7B:
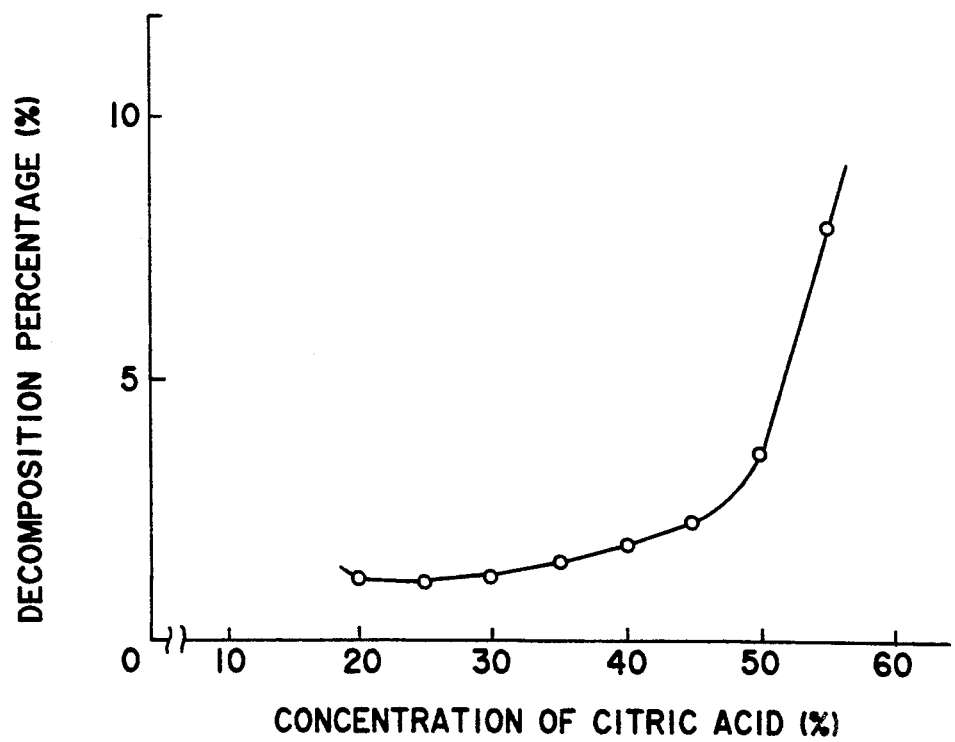
Figure 7C:
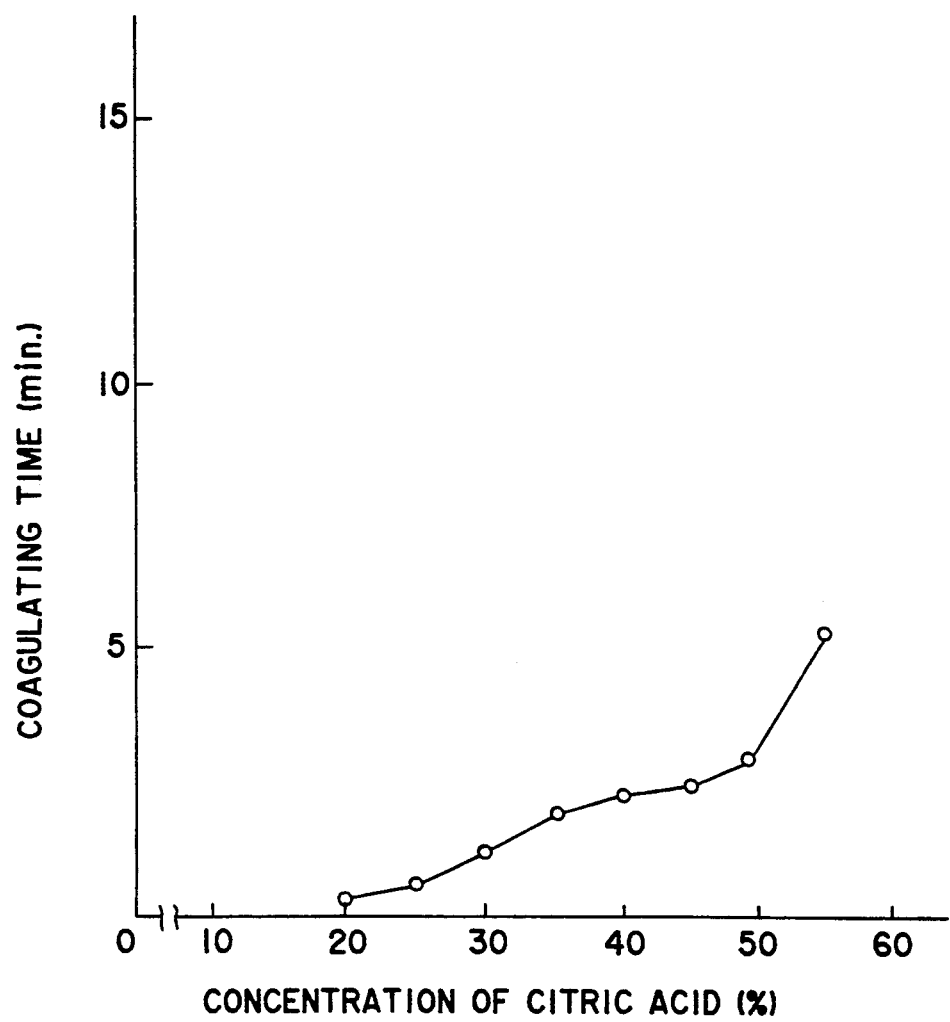

Each of FIGS. 8 to 12 are graphs representing variations of capacities against the ratio of powder to liquid in the respective examples, and in each Fig., (a) shows the variation of resisting force for crushing, (b) shows the variations of decomposition percentage, and each (c) shows the variation of coagulation time.

BEST MODE FOR CARRYING OUT THE INVENTION

Hereinafter examples in this invention are presented with examples for comparison purposes, but this invention is not limited within said examples.

EXAMPLES 1~31 AND EXAMPLES FOR COMPARISON 1~4

Solutions containing tannic acid, collagen, and organic acids in the concentration shown in Table 3 and 4 are prepared, and the solutions were mixed with calcium phosphate powder in the combinations also shown in Tables 3 and 4 and in a ratio of powder to liquid shown in Tables 3 and 4 and then, they were kneaded by hand for about one minute. The undermentioned measurements were carried out by using the kneaded mud and the results obtained are shown in Tables 3 and 4. Powder having an average particle diameter of 7 μm was used and aterocollagen (Cellmatrix LA produced from Nitta Gelatin Inc.) was used as the collagen. In addition, in the undermentioned measurements, all were carried out according to ADAS No. 61 under conditions that the temperature was 23°±2° C. and a relative humidity 50±10%. However, for the examples 1, 2, 14 and 19, the measurements according to ADAS No. 57 were carried out.

(a) Measurements of Time for Hardening at an Initial Stage

Each kneaded mud was poured into a metal mold of a cylinder shape and made of stainless steel, the mold having an inner diameter of 10 mm and a height of 5 mm. The mold was placed on a glass plate having a length, a width, and a thickness all 15 mm, and the surface was made even and, at one minute after the kneading was finished, the mud was transferred into a high temperature vessel showing a temperature of 37°±1° C. and humidity of 100% to prepare a piece for examination. The time when a bikkar needle having a weight of 2.94N (300 g) and a section area of 1 mm² is dropped on a surface of the piece for examination and a needle trace is not left, was assigned as the hardening time at an initial stage, calculated from the beginning of kneading. The hardening time at an initial stage was shown by taking an average of the values, obtained from three times measurements, by a 15 second unit.

TABLE 3

| | example 1 | example 2 | example 3 | example 4 | example 5 | example 6 | example 7 | example 8 | example 9 | example 10 |
|---|---|---|---|---|---|---|---|---|---|---|
| Combination of hardening materials for medical and dental use | | | | | | | | | | |
| Calcium phosphate powder (weight %) | | | | | | | | | | |
| 4CP | 100 | 100 | 100 | 100 | 100 | 100 | 100 | 80 | 80 | 80 |
| α-TCP | — | — | — | — | — | — | — | 20 | — | 10 |
| HAp | — | — | — | — | — | — | — | — | 20 | 10 |
| Solution composition (weight %) | | | | | | | | | | |
| tannic acid | 50 | 10 | 3 | 3 | — | — | 3 | 3 | — | 3 |
| collagen | — | 1 | — | — | 0.5 | 0.5 | 0.5 | — | 0.5 | 0.5 |
| malic acid | — | — | 40 | 40 | 40 | 40 | 40 | 40 | 40 | 40 |
| citric acid | — | — | 10 | — | 10 | — | 10 | 10 | 10 | 10 |
| malonic acid | — | — | — | 10 | — | 10 | — | — | — | — |
| Ratio between powder and liquid (g/ml) | 1.5 | 1.5 | 1.5 | 1.5 | 1.5 | 1.5 | 1.5 | 1.5 | 1.5 | 1.5 |
| Time for hardening at initial stage | 10 hr. or more | 24 hr. or more | 6 min. | 6 min. | 6 min. | 6 min. | 8 min. | 7.5 min. | 7.5 min. | 7 min. |
| Resisting force for crushing of hardened product at initial stage (kgf/cm²) | — | — | 920 | 920 | 950 | 950 | 1400 | 1100 | 950 | 1000 |

| | example 11 | example 12 | example 13 | example 14 | example 15 | example 16 | example 17 | example 18 | example for comparison 1 | example for comparison 2 |
|---|---|---|---|---|---|---|---|---|---|---|
| Combination of hardening materials for medical and dental use | | | | | | | | | | |
| Calcium phosphate powder (weight %) | | | | | | | | | | |
| 4CP | 20 | 100 | 80 | 80 | 100 | 100 | 80 | 80 | 80 | 80 |
| α-TCP | 80 | — | — | 20 | — | — | 20 | — | 20 | 20 |
| HAp | — | — | 20 | — | — | — | — | 20 | — | — |
| Solution composition (weight %) | | | | | | | | | | |
| tannic acid | 3 | 3 | — | 50 | — | — | — | — | — | — |
| collagen | — | — | 0.5 | — | — | — | — | — | — | — |
| malic acid | 40 | 40 | 40 | — | 40 | 40 | 40 | 40 | 50 | 40 |
| citric acid | 10 | 10 | 10 | — | 10 | 10 | 10 | 10 | — | — |
| malonic acid | — | — | — | — | — | — | — | — | — | — |
| Ratio between powder and liquid (g/ml) | 1.5 | 2.0 | 2.0 | 1.5 | 1.5 | 2.0 | 1.5 | 2.0 | 1.5 | 1.5 |
| Time for hardening at initial stage | 7 min. | 5 min. | 4.75 min. | 10 hr. or more | 4.5 min. | 3 min. | 3.5 min. | 2.25 min. | 3.5 min. | 3.0 min. |
| Resisting force for crushing of hardened product at initial stage (kgf/cm²) | 1200 | 1100 | 1100 | — | 900 | 950 | 900 | 950 | 850 | 900 |

(Note)
The residual part of solution is water.
The time for hardening for examples 1, 2, and 14 was determined according to ADA Specification No. 57.
The others were determined according to ADA Specification No. 61.

TABLE 4

| | example 19 | example 20 | example 21 | example 22 | example 23 | example 24 | example 25 | example 26 |
|---|---|---|---|---|---|---|---|---|
| Combination of hardening materials for medical and dental use | | | | | | | | |
| Calcium phosphate powder (weight %) | | | | | | | | |
| 4CP | — | — | — | — | — | — | — | — |
| α-TCP | 100 | 100 | 100 | 100 | 80 | 80 | 80 | 100 |
| HAp | — | — | — | — | 20 | 20 | 20 | — |
| Solution composition (weight %) | | | | | | | | |
| tannic acid | 10 | 3 | — | 3 | 3 | — | 3 | 3 |
| collagen | 1 | — | 0.5 | 0.5 | — | 0.5 | 0.5 | — |
| malic acid | — | — | — | — | — | — | — | — |
| citric acid | — | 45 | 45 | 45 | 45 | 45 | 45 | 45 |
| malonic acid | — | 7 | 7 | 7 | 7 | 7 | 7 | 7 |
| Ratio between powder and liquid (g/ml) | 2.0 | 2.0 | 2.0 | 2.0 | 2.0 | 2.0 | 2.0 | 3.0 |
| Time for hardening at initial stage | 24 hr. or more | 6 min. | 6 min. | 8 min. | 5.5 min. | 5.75 min. | 7.5 min. | 5.5 min. |
| Resisting force for crushing of hardened product at initial stage (kgf/cm$^2$) | — | 1120 | 1400 | 1500 | 1100 | 1350 | 1450 | 1700 |

| | example 27 | example 28 | example 29 | example 30 | example 31 | example for comparison 3 | example for comparison 4 |
|---|---|---|---|---|---|---|---|
| Combination of hardening materials for medical and dental use | | | | | | | |
| Calcium phosphate powder (weight %) | | | | | | | |
| 4CP | — | — | — | — | — | — | — |
| α-TCP | 80 | 100 | 100 | 80 | 80 | 100 | 100 |
| HAp | 20 | — | — | 20 | 20 | — | — |
| Solution composition (weight %) | | | | | | | |
| tannic acid | — | — | — | — | — | — | — |
| collagen | 0.5 | — | — | — | — | — | — |
| malic acid | — | — | — | — | — | — | — |
| citric acid | 45 | 45 | 45 | 45 | 45 | 52 | 45 |
| malonic acid | 7 | 7 | 7 | 7 | 7 | — | — |
| Ratio between powder and liquid (g/ml) | 3.0 | 2.0 | 3.0 | 2.0 | 3.0 | 2.0 | 2.0 |
| Time for hardening at initial stage | 5.5 min. | 4.5 min. | 3 min. | 4 min. | 2.5 min. | 4.5 min. | 3.5 min. |
| Resisting force for crushing of hardened product at initial stage (kgf/cm$^2$) | 1700 | 1100 | 1300 | 1000 | 1250 | 1050 | 1000 |

(Note)
The residual part of solution is water.
The time for hardening for example 19 was determined according to ADA Specification No. 57.
The others were determined according to ADA Specification No. 61.

(b) Measurements of Resisting Force for Crushing

Each kneaded mud was filled in a metal mold of a cylinder shape and made of stainless steel, the mold having an inner diameter of 6 mm and a height of 12 mm, and both its ends were pinched with thick glass plates and then, it was pressurized. At 2.5 minutes since the kneading was initiated, the mud was transferred while maintaining the pressurizing, into a thermostat which was kept at temperature of 37°±1° C., and taken out from the distilled water after the time passage of 24 hours since the kneading was initiated, to use it was a piece for examination. This piece for examination was subjected to measurements of resisting force for crushing with use of a Shimazu Autograph AG-2000 A. At a cross-head speed of 1 mm per minute, the measurements were carried out with six pieces for examination and the value measured was obtained by averaging the numerical values which remained after removal of the values showing −15% or less of the total average value. But, when two or more of the values showing −15% or less of the total average value existed, the measurements were carried out again.

As seen in Tables 3 and 4, the materials in the examples 1, 2, 14, and 19 proceeded with the hardening process at the initial stage slower than the case where an organic acid was used as a hardening adjuster, so that they are better suited for sealing a root canal. Comparing the examples 3~13 and 15~18 with the examples for comparison 1 and 2 and also, the examples 20~31 with the examples for comparison 3 and 4, the examples showed longer hardening time at the initial stage. In addition, since a setting solution containing one or more kinds of organic acids is used for the examples for comparison 1~4, in order to delay the hardening time, the concentration may be enhanced or the ratio between powder and liquid may be lower. However, if the concentration of the setting solution was enhanced, greater force was required for kneading, and if the ratio between powder and liquid was lowered, the resisting force for crushing at an initial stage tended to be lower. Even though, as shown in the examples 12, 13, 26, and 27, the ratio between powder and liquid was enhanced and the resisting force for crushing of the hardened product was enhanced, the hardening time at an initial stage was of such a length that it was practically no problem. However, in the examples 16, 18, 29, and 31, with enhancement of the ratio between powder and liquid, the hardening time at an initial stage became extremely short.

Also, in the cases that collagen was used (examples 5~7, 9, 10, 13, 21, 22, 24, 25 and 27), the resisting force for crushing at an initial stage clearly increased and, in particular, the case where tannin was used in combination showed specially enhanced performance.

When each of the materials in the examples 3~13, 15~18, and 20~31, and the examples for comparison 1~4 was immersed in PBS, the cases where collagen was used showed that, even after the hardening at the initial stage, the resisting force for crushing was increasing with the passage of time.

In addition, each material in the examples 3~13, 15~18, and 20~31 was hardened at an initial stage to a piece of cylindrical shape of $\phi$ 6 mm×length 12 mm, buried in a defective part of a femur of a dog, taken out after standing, respectively, for 2, 4, and 6 weeks, and evaluated by tissue observation at a surface conjugated with a bone tissue and by a pushing-out method which is to observe the conjugation force with the bone. As a result, in the cases of materials in the examples 15~18 and 28~31, although a direct conjugation with the bone was initiated, a slight degree of cell infiltration of a circular shape was observed Also, in each material of the examples 3~13 and 20~27, no inflammatory reaction of such a kind was found a direct conjugation with a bone already progressed. When the materials of examples 15~18 and 28~31 stood for 4 and 6 weeks after transplantation, the inflammatory symptoms gradually disappeared and gradually increasing bond-formation in this part was observed. In each material of the examples 3~13 and 20~27, there existed bone cells in an interface with the bone tissue. Especially, in the cases where collagen was used (examples 5~7, 9, 10, 13, 21, 22, 24, 25 and 27), a number of bone cells existed in the circumference of the interface and the rigidly conjugating force with a bone increased by leaps and bounds.

EXAMPLE 32

Prepared was a hardening material composed of a powder agent which contained 80% of 4CP and 20% of α-TCP, and a setting solution (a liquid agent) which was made by dissolving into water a composition composed of 40% of malic acid, 10% of citric acid, and 5% of gluconic acid. In this example, the malic acid, citric acid, and gluconic acid are hardening adjusters.

EXAMPLE 33

Prepared was a hardening material composed of a powder agent which contained 80% of 4CP and 20% of α-TCP, and a setting solution (a liquid agent) which was made by dissolving into water a composition composed of 40% of malic acid, 10% of citric acid, and 5% of lactic acid.

In this example the malic acid, citric acid, and lactic acid are hardening agents.

EXAMPLE 34

Prepared was a hardening material composed of a powder agent which contained 80% of 4CP and 20% of α-TCP, and a setting solution (a liquid agent) which was made by dissolving into water malic acid, citric acid, and acid-soluble collagen (Cellmatrix type I-A produced from Nitta Gelatin Inc., which converts into fibrils within 8 minutes under physiological conditions) in their respective proportions of 40, 10, and 0.5%. In this example the malic acid, citric acid, and collagen are hardening adjustors.

EXAMPLE 35

Prepared was a hardening material composed of a powder agent which contained 80% of 4CP and 20% of α-TCP, and a setting solution (a liquid agent) which was made by dissolving into water malic acid, citric acid, the type II collagen (Cellmatrix type II produced from Nitta Gelatin Inc., which does not convert into fibrils under physiological conditions), and decomposed gelatin (water-soluble gelatin produced from Nitta Gelatin Inc., which does not convert into fibrils under physiological conditions) in their respective proportions of 40, 10, 0.5, and 1%. In this example the malic acid, citric acid, type II collagen, and decomposed gelatin are hardening adjusters.

EXAMPLE 36

Prepared was a hardening material composed of a powder agent, which was composed of 78% of 4CP, 20% of α-TCP, and 2% of zinc tannate, and a setting solution (a liquid agent) which was made by dissolving into water malic acid and citric acid in their respective proportions of 40% and 10%. In this example the malic acid, citric acid, and zinc tannate are hardening adjusters.

EXAMPLE 37

Prepared was a hardening material composed of a powder agent, which was composed of 75% of 4CP, 20% of α-TCP, and 5% of albumin tannate, and a setting solution (a liquid agent) which was made by dissolving into water malic acid and citric acid in their respective proportions of 40 and 10%. In this example the malic acid, citric acid, and albumin tannate are hardening adjusters.

EXAMPLE 38

Prepared was a hardening material composed of a powder agent, which was composed of 34.6% of α-TCP, 20.4% of 4CP, 28.0% of HAp, 2% of $TiO_2$, 10% of $BaSO_4$, 0.5% of β-carotene, 2% of bismuth pyrogallate, 0.5% of MgO, and 2% of calcium citrate, and a setting solution (a liquid agent) which was made by dissolving into water citric acid, malonic acid, malic acid, gluconic acid, chitosan, carboxymethylchitin, jellan gum, polyalkylene glycol, polyphosphoric acid, tannic acid, aterocollagen (Cellmatrix produced from Nitta Gelatin Inc., which converts into fibrils with a time longer than 8 minutes under physiological conditions), glycolic acid, pyruvic acid, and phytic acid in their respective proportions of 1.0, 2.0, 2.0, 2.0, 1.0, 1.0, 1.0, 1.0, 0.5, 15, 2, 0.5, 0.5, 0.5, and 0.5%. In this example the bismuth pyrogallte, citric acid, malonic acid, malic acid, gluconic acid, tannic acid, aterocollagen, glycolic acid, pyruvic acid, and phytic acid are hardening adjusters.

Each hardening material in the examples 32~38 was mixed in the ratio of powder to liquid shown in Table 5 and kneaded as carried out in the example I and then, the time for hardening at the initial stage and the resisting force for crushing were examined as carried out in the example 1. Results are presented in Table 5.

The capacities do not decrease and, as shown in Table 5, the time for hardening at the initial state was adjusted (refer to the examples for comparison 1 and 2 in Table 3 and the example 17)

Hereinafter, concrete examples and examples for comparison for the hardening materials relating to the inventions in claims 9, 10, 13, and 14 are shown, but the inventions are not limited within the below-described examples.

The powder used had an averaged particle diameter in a range of 1~20 μm.

EXAMPLES 39~49 AND EXAMPLES FOR COMPARISON 5 AND 6

The hardening materials were prepared with the combination shown in Table 6.

EXAMPLES 49~54 AND EXAMPLES FOR COMPARISON 7 AND 8

The hardening materials were prepared with the combination shown in Table 7.

For the hardening materials in said examples and examples for comparison, the powder and the liquid were mixed and kneaded under room temperature and the resisting force for crushing, decomposition percentage, and coagulating time were determined according to JIS T6602. Results are shown in Tables 6 and 7 together with the combination ratio in the hardening materials.

As seen in Tables 6 and 7, the hardening materials in the examples produced hardened products of high resisting force for crushing and low decomposition percentage, and their coagulating time was properly slow.

In the examples for comparison, sometimes the resisting force for crushing was small, the decomposition percentage was large, and the coagulation time was too short or too long.

EXAMPLE 55

Prepared was a hardening material composed of a setting solution, which was prepared by dissolving citric acid and malonic acid in their respective proportions of 39 and 6% into water, and α-TCP.

EXAMPLE 56

Prepared was a hardening material composed of a setting solution, which was prepared by dissolving malic acid and citric acid in their respective proportions of 36 and 9% into water and α-TCP.

TABLE 5

|  | powder/liquid ratio (g/ml) | time for hardening at initial stage | resisting force for crushing of hardened product at initial stage [kgf/cm²] |
|---|---|---|---|
| example 32 | 1.5 | 8.0 min. | 900 |
| example 33 | 1.5 | 5.0 min. | 900 |
| example 34 | 1.5 | 4.5 min. | 1000 |
| example 35 | 1.5 | 5.0 min. | 900 |
| example 36 | 1.5 | 6.0 min. | 1000 |
| example 37 | 1.5 | 4.5 min. | 900 |
| example 38 | 1.5 | 120 min. | 110 |

TABLE 6

|  | example 39 | example 40 | example 41 | example 42 | example 43 | example 44 | example 45 | example 46 | example 47 | example 48 | example for comparison 5 | example for comparison 6 |
|---|---|---|---|---|---|---|---|---|---|---|---|---|
| combination of hardening materials | | | | | | | | | | | | |
| powder agent (%) | | | | | | | | | | | | |
| α-TCP | 100 | 100 | 100 | 100 | 100 | 100 | 100 | 80 | 80 | 63 | 100 | 63 |
| 4CP | — | — | — | — | — | — | — | 20 | 20 | 37 | — | 37 |
| total concentration of organic acids in setting solution (%) | 45 | 45 | 45 | 45 | 45 | 45 | 45 | 47 | 47 | 45 | 45 | 45 |
| **proportion for use of organic acids*1 (parts)** | | | | | | | | | | | | |
| citric acid | 65 | 85 | 85 | 60 | 70 | 75 | 89 | 70 | 89 | 65 | 55 | 40 |
| malonic acid | 35 | 15 | — | 30 | 20 | — | — | — | — | 20 | 45 | 10 |
| tannic acid | — | — | 15 | 10 | 10 | 25 | 11 | 30 | 11 | 15 | — | 50 |
| powder/liquid ratio (g/ml) | 2.5 | 2.5 | 2.5 | 2.5 | 2.5 | 2.5 | 2.5 | 2.6 | 2.6 | 2.3 | 2.5 | 2.0 |
| resisting force for crushing (kgf/cm²) | 1350 | 1500 | 1500 | 1500 | 1600 | 1250 | 1400 | 1250 | 1500 | 1350 | 1600 | 450 |
| decomposition percentage (%) | 2.0 | 1.7 | 1.6 | 1.6 | 1.7 | 1.7 | 2.0 | 1.6 | 1.8 | 1.8 | 4.5 | 5.0 |
| coagulating time (min.) | 4.5 | 3.5 | 4.5 | 4.5 | 4.0 | 6.0 | 7.0 | 4.5 | 5.0 | 5.0 | 6.0 | 50 |

*1 proportion against 100 parts of total organic acids (part)

TABLE 7

|  | example 49 | example 50 | example 51 | example 52 | example 53 | example for comparison 7 | example for comparison 8 | example 54 | example for comparison 9 |
|---|---|---|---|---|---|---|---|---|---|
| combination of hardening materials | | | | | | | | | |
| powder agent (%) | | | | | | | | | |

TABLE 7-continued

|  | example 49 | example 50 | example 51 | example 52 | example 53 | example for comparison 7 | example for comparison 8 | example 54 | example for comparison 9 |
| --- | --- | --- | --- | --- | --- | --- | --- | --- | --- |
| α-TCP | 100 | 100 | 100 | 100 | 100 | 100 | 100 | 63 | 63 |
| 4CP | — | — | — | — | — | — | — | 37 | 37 |
| total concentration of organic acids in setting solution (%) | 45 | 45 | 45 | 45 | 45 | 45 | 45 | 45 | 45 |
| proportion for use of organic acids*1 (parts) |  |  |  |  |  |  |  |  |  |
| citric acid | 65 | 10 | — | 65 | 30 | 75 | — | 65 | 10 |
| malic acid | 35 | 90 | 90 | 20 | 60 | 25 | 75 | 20 | 40 |
| tannic acid | — | — | 10 | 15 | 10 | — | 25 | 15 | 50 |
| powder/liquid ratio (g/ml) | 2.5 | 2.5 | 2.5 | 2.5 | 2.5 | 2.5 | 2.5 | 2.3 | 2.3 |
| resisting force for crushing (kgf/cm$^2$) | 1550 | 1450 | 1400 | 1550 | 1550 | 1550 | 1250 | 1350 | 400 |
| decomposition percentage (%) | 2.0 | 2.0 | 2.0 | 1.8 | 1.8 | 2.5 | 2.5 | 1.8 | 5.5 |
| coagulating time (min.) | 3.0 | 5.0 | 6.0 | 4.0 | 6.0 | 1.8 | 8.5 | 4.0 | 60 |

*1 proportion against 100 parts of total organic acids (part)

EXAMPLE 57

Prepared was a hardening material composed of a setting solution, which was prepared by dissolving citric acid, malonic acid, and tannic acid in their respective proportions of 35, 5, and 5% into water, and α-TCP.

EXAMPLE 58

Prepared was a hardening material composed of a setting solution, which was prepared by dissolving malic acid, citric acid, and tannic acid in their respective proportions of 32, 8, and 5% into water and α-TCP.

EXAMPLE 59

Prepared was a hardening material composed of a powder agent 15 which contained 47.2% of α-TCP, 27.8% of 4CP, 7% of HAp, 2% of TiO$_2$, 10% of BaSo$_4$, 1% of CaF$_2$, 0.5% of β-carotene, 2% of bismuth pyrogallate, 0.5% of MgO, and 2% of calcium citrate, and a setting solution (a liquid agent) which was prepared by dissolving citric acid, malonic acid, malic acid, gluconic acid, chitosan, jellan gum, polyalkylene glycol, polyphosphoric acid, tannic acid, alterocollagen (Cellmatrix LA produced from Nitta Gelatin Inc., which converts into fibrils in a time longer than 8 minutes under physiological conditions), glycolic acid, pyruvic acid, and phytic acid in their respective proportions of 32, 1, 5.4 1.3, 0.1, 0.5, 0.5, 0.5, 4.5, 0.5, 0.5, 0.1 and 0.5% into water. In this example, the bismuth pyrogallate, citric acid, malonic acid, malic acid, gluconic acid, tannic acid, aterocollagen, glycolic acid, pyruvic acid, and phytic acid are hardening adjusters.

EXAMPLE 60

Prepared was a hardening material composed of a powder agent which contained 47.2% of α-TCP, 27.8% of 4CP, 7% of HAp, 2% of TiO$_2$, 10% of BaSO$_4$, 1% of CaF$_2$, 0.5% of β-carotene, 2% of bismuth pyrogallate, 0.5% of MgO, and 2% of calcium citrate, and a setting solution (a liquid agent) which was prepared by dissolving citric acid, malic acid, gluconic acid, chitosan, jellan gum, polyalkylene glycol, polyphosphoric acid, aterocollagen (Cellmatrix LA, produced from Nitta Gelatin Inc.: which converts into fibrils taking a time longer than 8 minutes under a physiological condition.), glycolic acid, pyruvic acid, and phytic acid in their respective proportions of 42%, 1.3%, 0.1%, 0.5%, 0.5%, 0.5%, 0.5% 0.5%, 0.5%, 0.1%, 0.5% into water. In this example, bismuth pyrogallate, citric acid, malic acid, gluconic acid, aterocollagen, glycolic acid, pyruvic acid, and phytic acid are hardening adjusters.

EXAMPLE 61

Prepared was a hardening material composed of a powder agent which contained 47.2% of α-TCP, 27.8% of 4CP, 7% of HAp, 2% of TiO$_2$, 10% of BaSO$_4$, 1% of CaF$_2$, 0.5% of β-carotene, 2% of bismuth pyrogallate, 0.5% of MgO, and 2% calcium citrate, and a setting solution (a liquid agent) which was prepared by dissolving citric acid, malic acid, gluconic acid, chitosan, jellan gum, polyalkyleneglycol, polyphosphoric acid, aterocollagen (Cellmatrix LA, produced from Nitta Gelatin Inc., which converts into fibrils taking a time longer than 8 minutes under a physiological condition.), glycolic acid, pyruvic acid and phytic acid in their respective proportions of 32.1%, 1.3%, 0.1%, 0.5%, 0.5%, 0.5%, 0.5%, 0.5%, 0.5%, 0.1% and 0.5% into water. In this example, bismuth pyrogallate, citric acid, malic acid, gluconic acid, aterocollagen, glycolic acid, pyruvic acid, and phytic acid are hardening adjusters.

Variation of the resisting force for crushing, the decomposition percentage, and the coagulating time were investigated when the powder to liquid ratio of each hardening material in the example 55∼61 was changed. For comparison, taking 45%, 39%, and 35% aqueous solutions of citric acid (regarding the examples 55 and 57) and 45%, 36%, and 32% aqueous solutions of malic acid (regarding the examples 56 and 58) as setting solutions and α-TCP, variations of the resisting force for crushing, the decomposition percentage, and the coagulating time were investigated. Results were showed in FIGS. 8 (example 55), 9 (example 56), 10 (example 57), 11 (example 58), and 12 (example 59∼61), respectively. In FIGS. 8-12, the figures (a) show variation of the resisting force for crushing (kg f/cm$^2$), the figures (b) show the decomposition percentage (%), and the figures (c) show the coagulating time (min.). In FIGS. 8-11, a curved line connecting the black circles is for the examples and curved lines connecting the opened circles and the triangles are, respectively, for examples in which an aqueous solution of only citric acid or an aqueous solution of only malic acid is the setting solution. Also, in FIG. 12, a curved line connecting the black circles is for example 59, a curved line connecting the opened circles for example 60, and a curved line connecting the triangles for example 61.

Figure 8A:
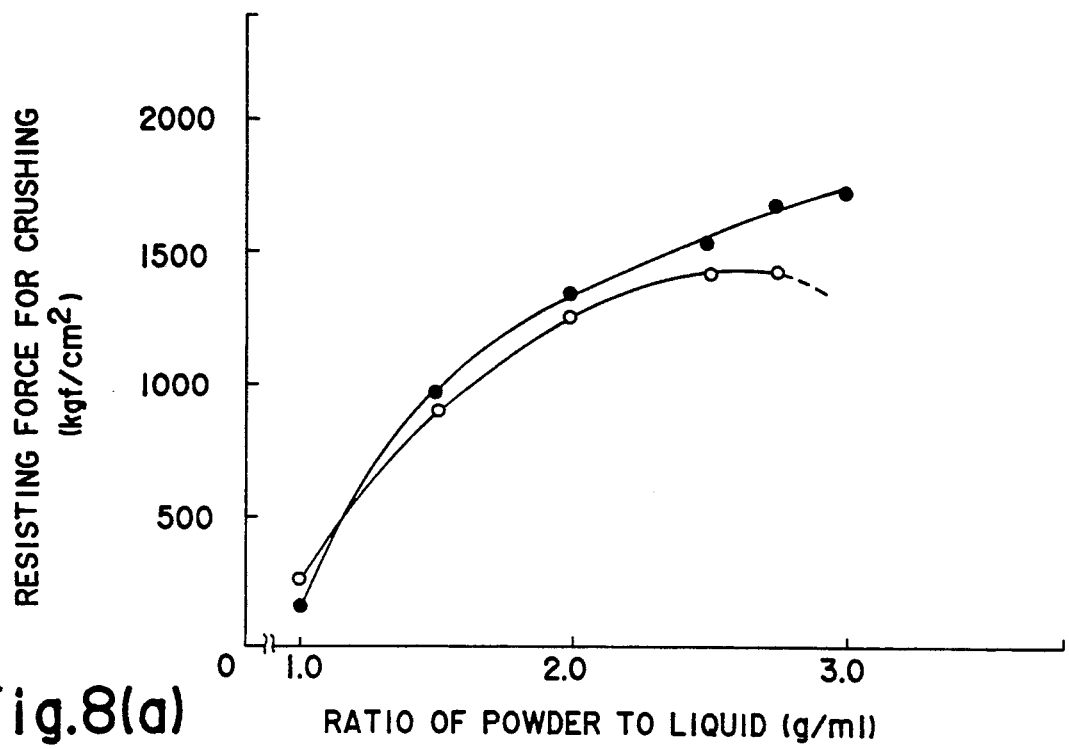
Figure 8B:
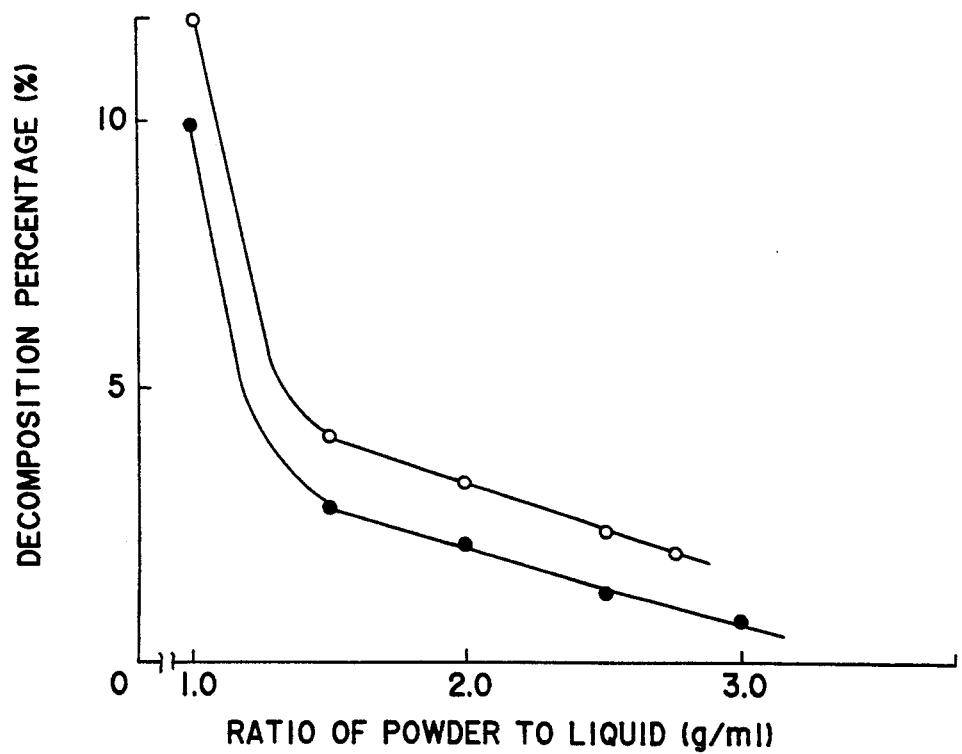
Figure 8C:
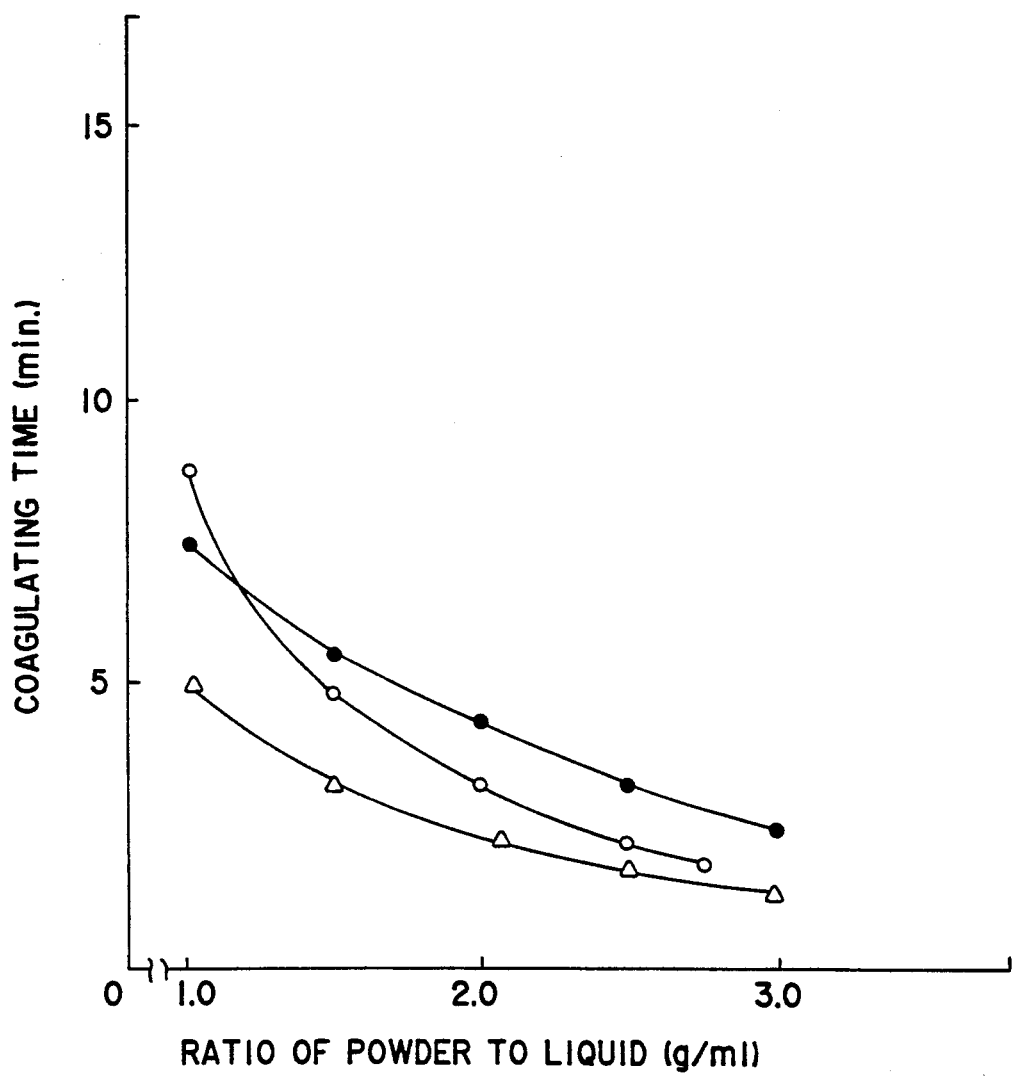
Figure 9A:
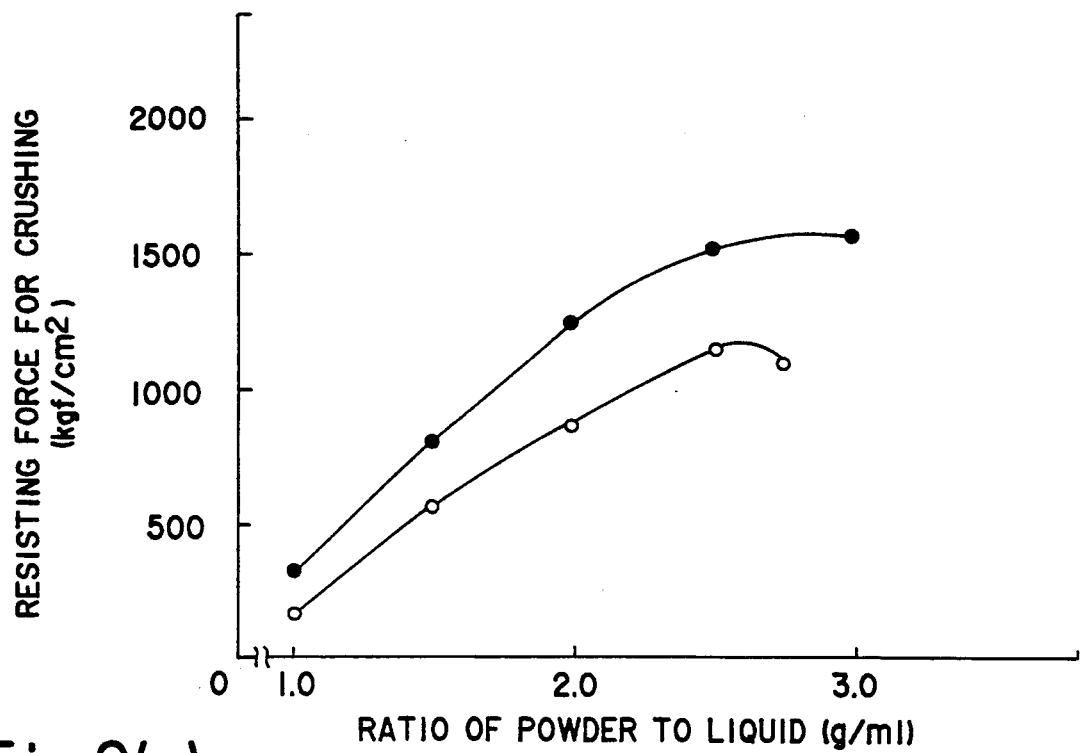
Figure 9B:
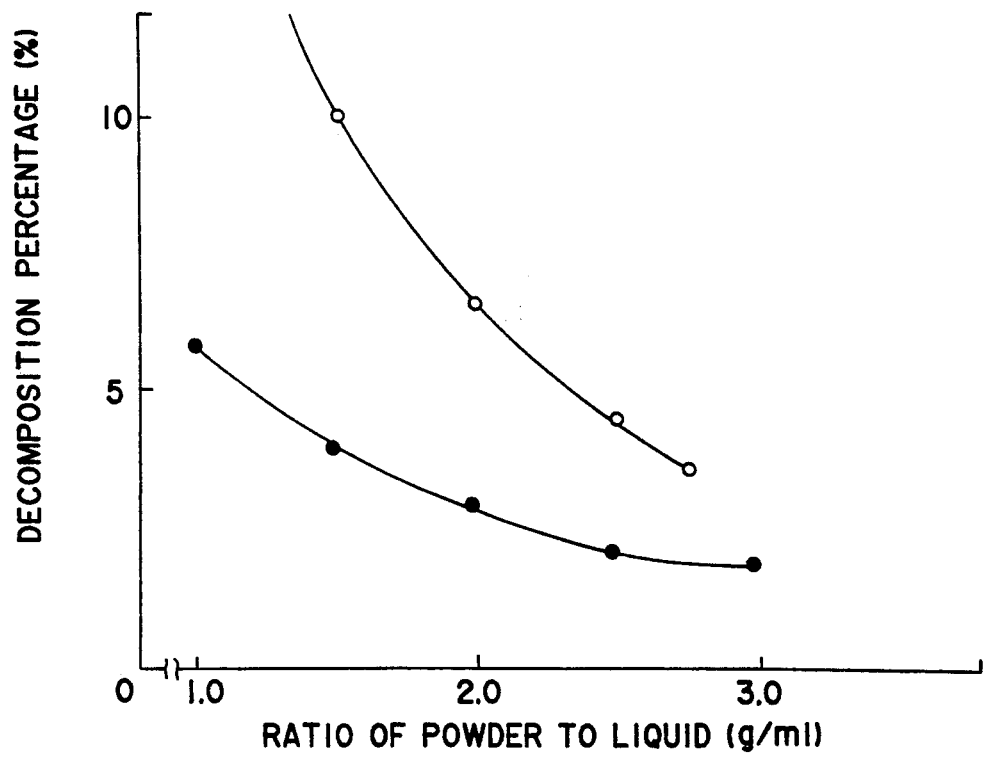
Figure 9C:
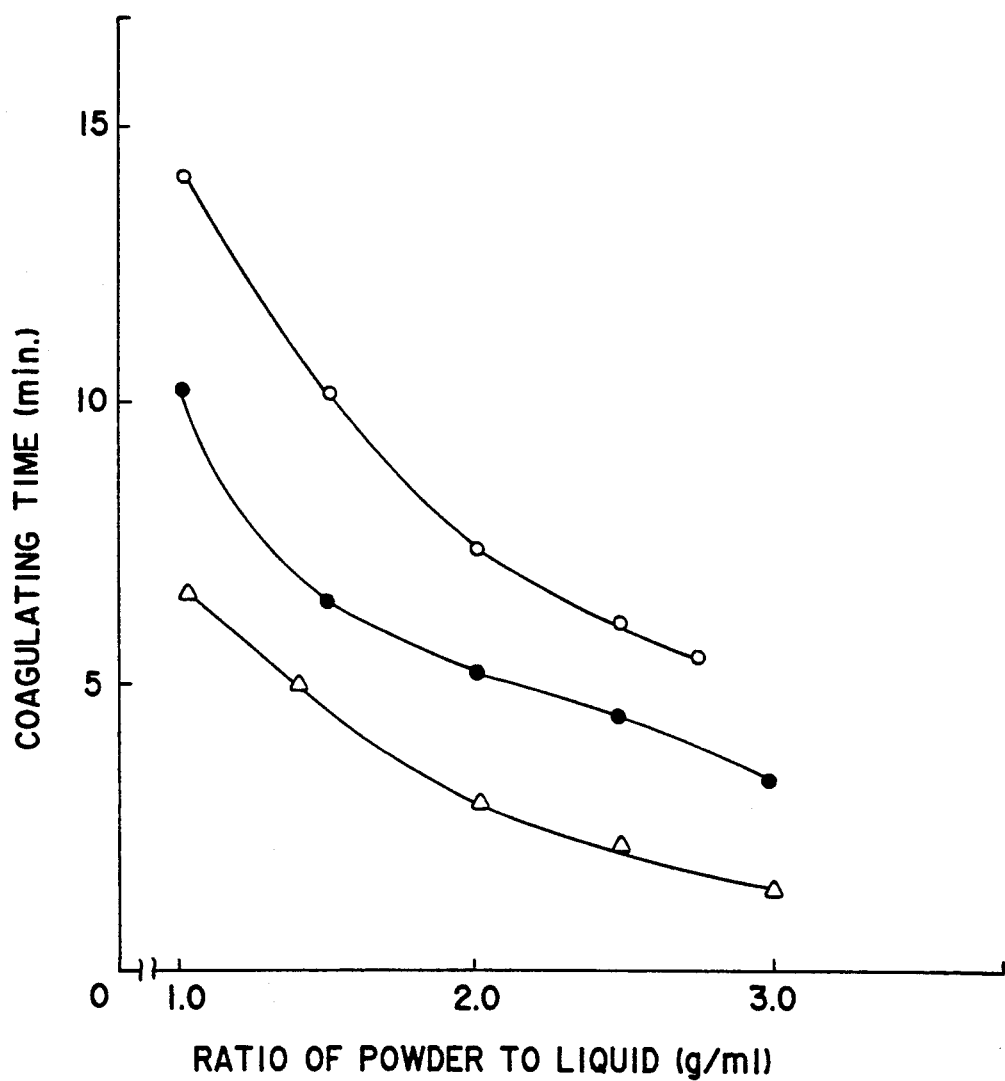
Figure 10A:
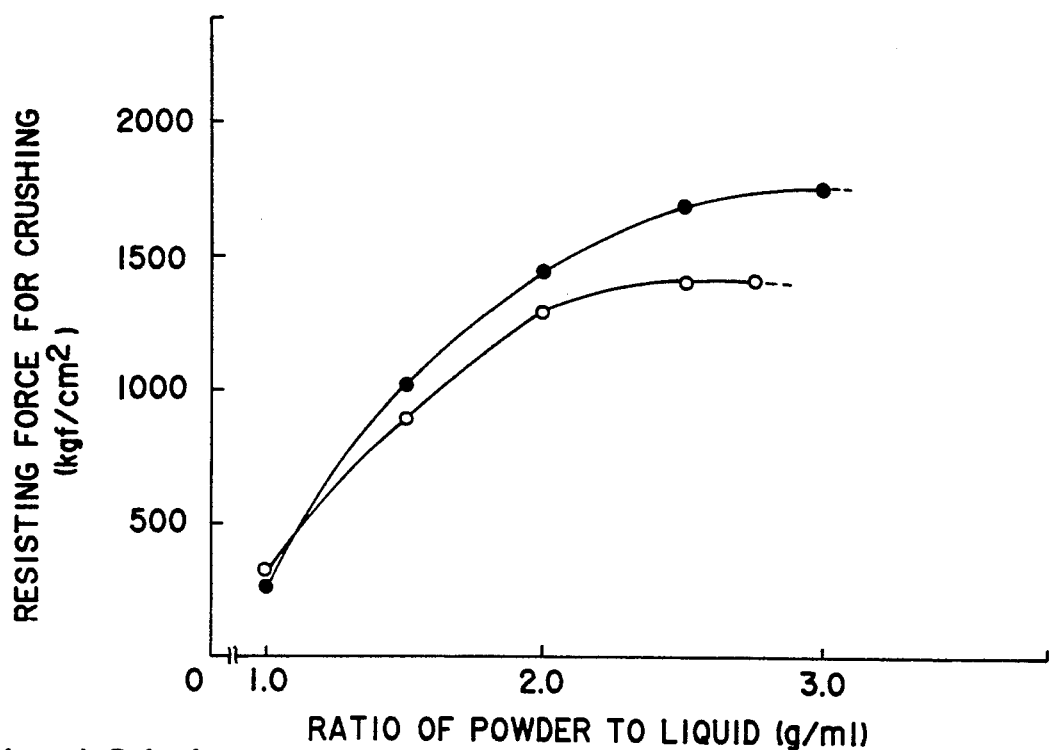
Figure 10B:
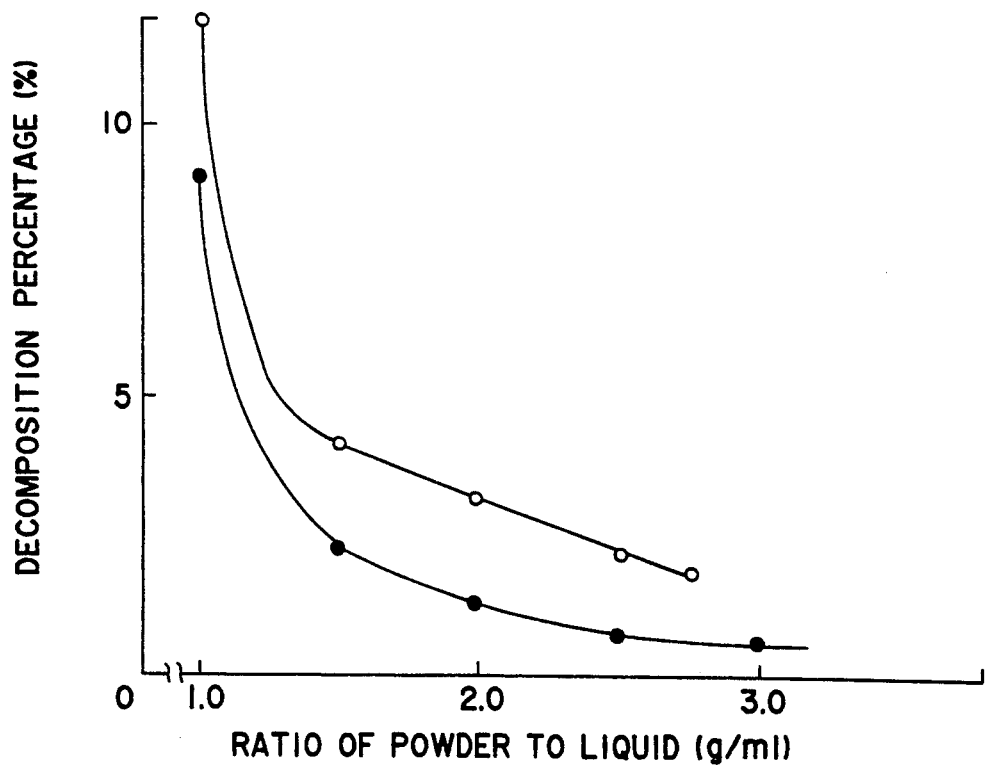
Figure 10C:
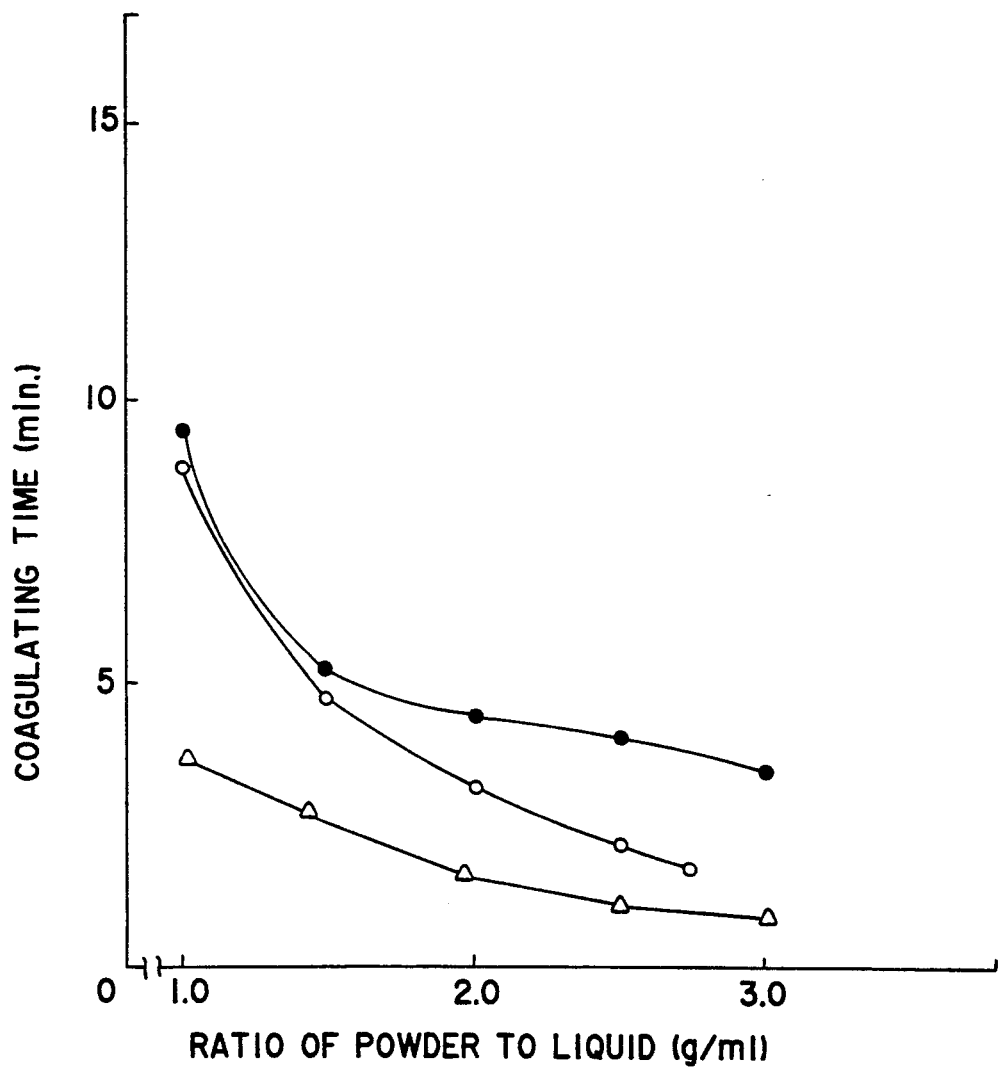
Figure 11A:
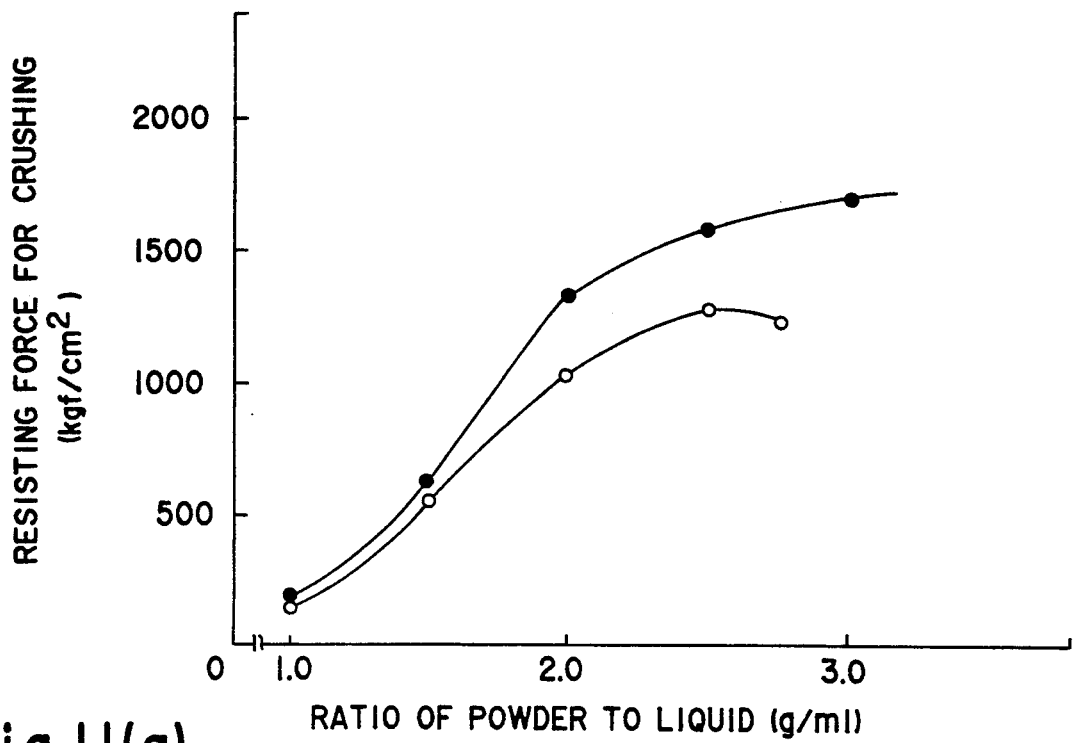
Figure 11B:
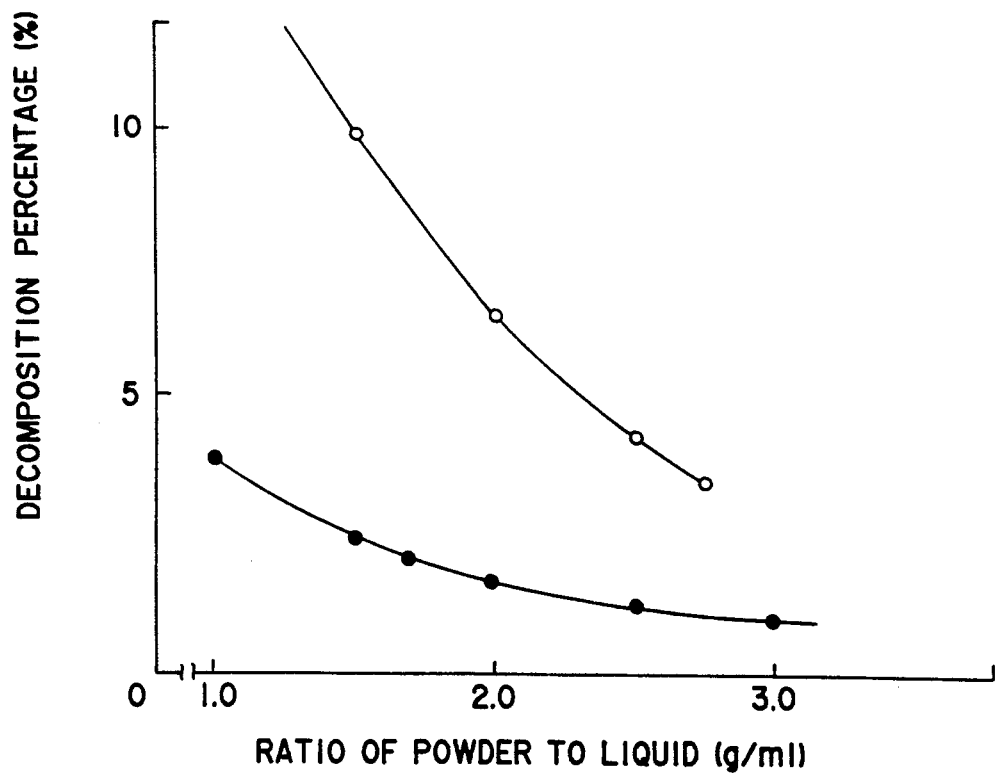
Figure 11C:
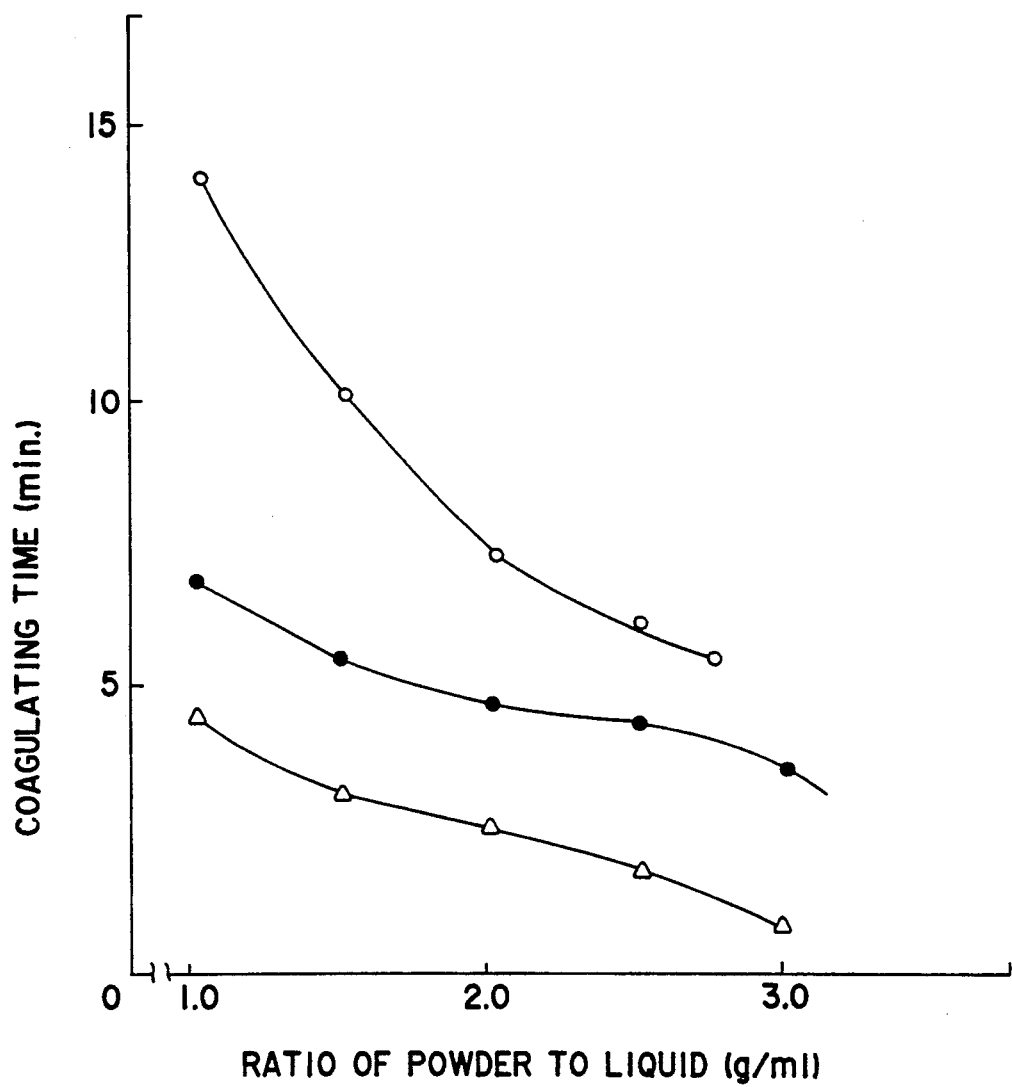
Figure 12A:
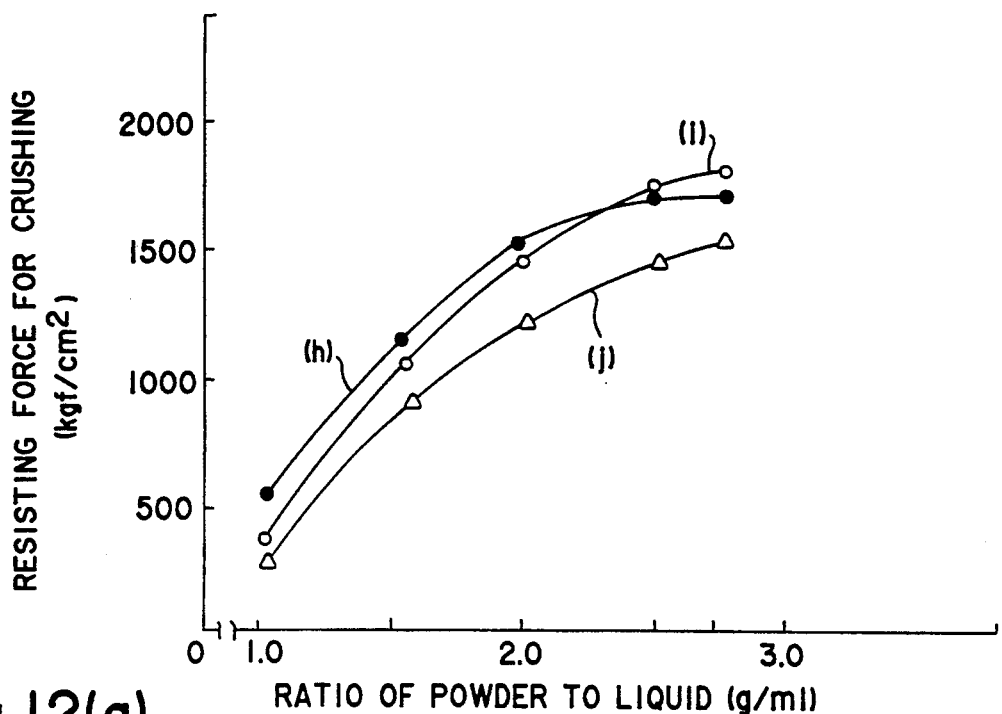
Figure 12B:
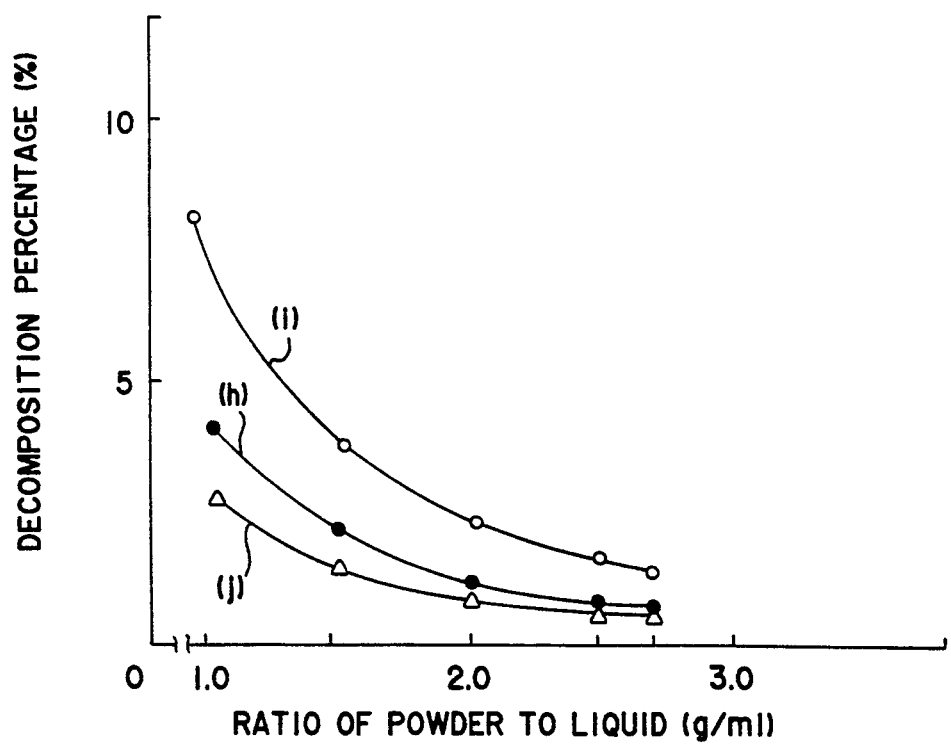
Figure 12C:
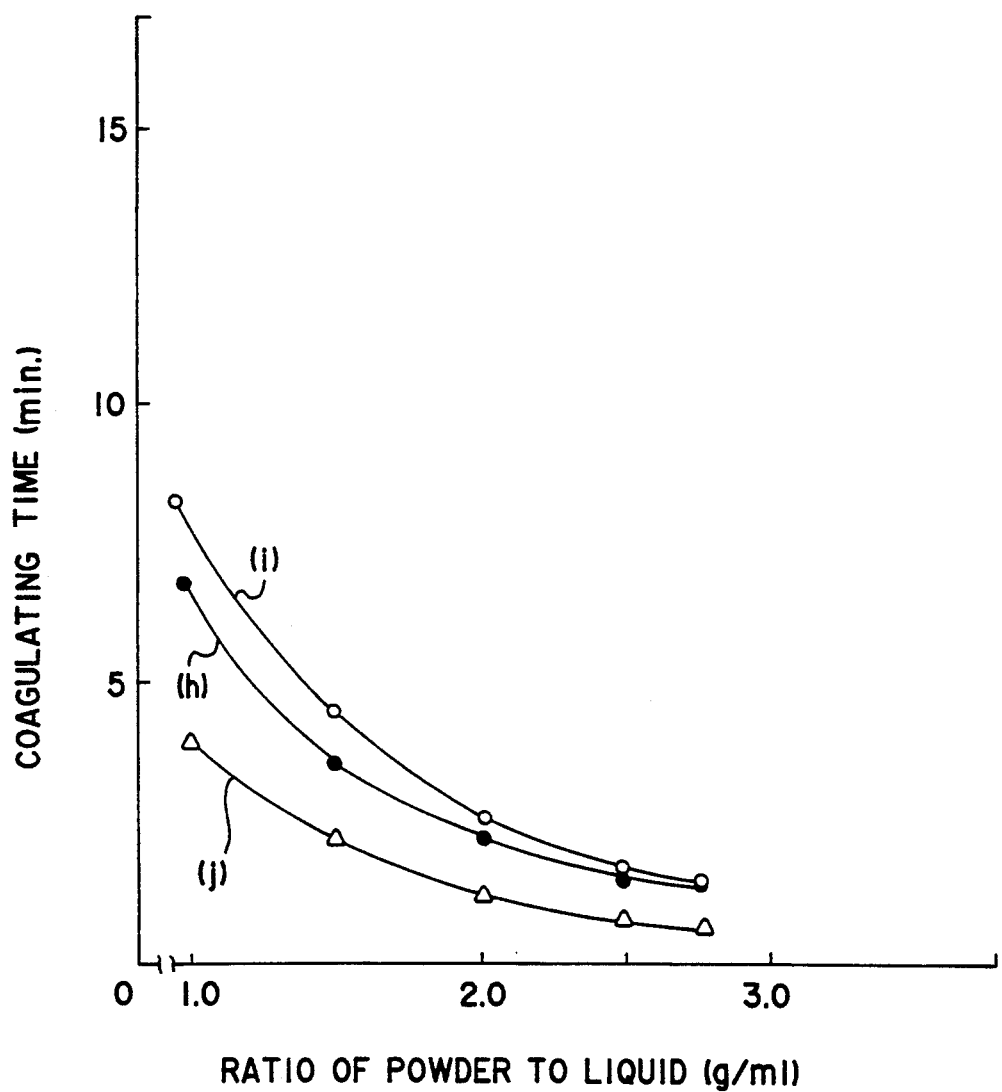

As seen in FIGS. 8~1, respectively, the hardening materials in the inventions as claimed in claims 9, 10, 13 and 14 show relatively small variation of capacities with the changing powder to liquid ratio. Also, as seen in FIG. 12, when the case where citric acid, malonic acid, and tannic acid are defined in said special combination proportion (example 59) is compared with the which deviates from the defined combination proportion, the resisting force for crushing varied to a higher direction, the decomposition percentage to a smaller direction, and the coagulating time to a longer direction. That is, it is seen that, even if another component is added to said defined combination proportion, the good physical properties are still displayed.

Examples in the case of where hardening materials in the present invention are used for a root canal sealer are shown hereinafter with examples for comparison.

EXAMPLE 62

Prepared was a hardening material composed of a powder agent of 100% of α-TCP and a setting solution (a liquid agent) which was prepared by dissolving citric acid and tannic acid in their respective proportions of 22.5% and 22.5% into water.

EXAMPLE 63

Prepared was a hardening material composed of a powder agent of 100% of α-TCP and a setting solution (a liquid agent) which was prepared by dissolving citric acid and tannic acid in their respective proportions of 13% and 32% into water.

EXAMPLE 64

Prepared was a hardening material composed of a powder agent of 100% of 4CP and a setting solution (a liquid agent) which was prepared by dissolving citric acid and tannic acid in their respective proportions of 8% and 22% into water.

EXAMPLE 65

Prepared was a hardening material composed of a powder agent which contained 63% of α-TCP and 37% of 4CP, and a setting solution (a setting liquid) which was prepared by dissolving citric acid and tannic acid in their respective proportions of 2% and 5% into water.

EXAMPLE 66

Prepared was a hardening material composed of a powder agent which contained 44% of α-TCP, 26% of 4CP, 10% of bismuth pyrogallate, and 20% of $BaSO_4$, and a setting solution (a liquid agent) which was prepared by dissolving citric acid and tannic acid in their respective proportions of 2% and 5% into water.

EXAMPLE 67

Prepared was a hardening material composed of a powder agent which contained 98% of 4CP and 2% of carboxymethylchitin, and a setting solution (a liquid agent) which was prepared by dissolving aterocollagen (Cellmatrix LA, produced from Nitta Gelatin Inc.), malic acid, and citric acid in their proportions of 0.5%, 18%, and 4.5% into water.

EXAMPLE 68

Prepared was a hardening material composed of a powder agent of 100% of 4CP and a setting solution (a liquid agent) which was prepared by dissolving alginic acid, malic acid, and citric acid into their respective proportions of 0.5%, 18%, and 4.5% into water.

EXAMPLE 69

Prepared was a hardening material composed of a powder agent which contained 95% of 4CP and 5% of aterocollagen (Cellmatrix LA, produced from Nitta Gelatin Inc.), and a setting solution (a liquid agent) which was prepared by dissolving alginic acid, malic acid, and citric acid in their respective proportions of 0.5%, 18% and 4.5% into water.

EXAMPLE 70

Prepared was a hardening material composed of a powder agent of 100% of 4CP and a setting solution (a liquid agent) which was prepared by dissolving xanthan gum, malic acid, and citric acid in their proportions of 0.3%, 15%, and 3.7% into water.

EXAMPLE 71

Prepared was a hardening material composed of a powder agent of 100% of 4CP and a setting solution (a liquid agent) which was prepared by dissolving aterocollagen (Cellmatrix LA, produced from Nitta Gelatin Inc.), xanthan gum, malic acid, and citric acid in their respective proportions of 0.3%, 0.3%, 5%, and 3.7% into water.

EXAMPLE FOR COMPARISON 10

Prepared was a root canal sealer composed of a powder agent which contained 20% of 4CP, 20% of 4CP, 20% of MgO, 20% of rosin, and 40% of bismuth bicarbonate, and a solvent composed of 100% of oleic acid.

EXAMPLE FOR COMPARISON 11

Prepared was a root canal sealer composed of a powder agent which contained 43% of 4CP, 20% of MgO, 30% of bismuth bicarbonate, and 0.7% of $Ca(OH)_2$, and a solvent composed of 100% of euginol.

EXAMPLE FOR COMPARISON 12

Used was a root canal sealer commercially available from Showa Yakuhin Kagaku Kogyo Co., Ltd. under the tradename Kyanarusu.

For the materials in the examples 62~71 and the examples for comparison 10~12, according to the ISO standards (International Organization for Standardization) 6876-1986 (E), the flow (a degree of flowing with pressure), a time for hardening, solubility, degree of decomposition (referred to as "decomposition percentage"), and resisting force for crushing were determined. In addition, using an aqueous solution in which the decomposition percentage was already determined, tannic acid eluded was confirmed with a colorimeter. Furthermore, cement or a root canal sealer was filled with pressure in a place where a molar dental pulp of a grown dog was extracted and then, stood for 3 months. Tooth extraction was followed by setting and then, a slice for polishing which did not decalcificate was subjected to a pathological observation with haematoxyline-eosine (referred to as "H-E") coloring.

1) Flow (degree of flowing with pressure:

A root canal sealer was kneaded, 0.075 ml is placed on a glass plate and, at 3 minutes after the kneading is initiated, a load of 2.5% kg is imposed. Then, the flow is determined by the diameter of the spread kneaded mud.

According to the ISO standards, the value is defined as 20 mm or more.

2) Time for hardening;

A kneaded mud is filled in a ring having a diameter of 10 mm and a height of 2 mm and the time that, at 2 minutes after the kneading is initiated, a Gilmore needle having a load of 100 g and a diameter of 2 mm does not give a pressed trace under the conditions of ordinary temperature of 37° C. and relative humidity of 95% or more, is defined as the time for hardening.

3) Solubility and decomposition degree (decomposition percentage);

A kneaded mud is filled in a ring having a diameter of 20 mm and a thickness of about 1.5 mm and, under the conditions of room temperature of 37° C. and relative humidity of 95% or more is allowed to stand for hardening for a time that is 1.5 times of a time for hardening of each cement, whereby a slice for examination is obtained. This slice is immersed in 50 ml of distilled water at 37° C. for 24 hours and then, the water in a stoppered bottle is evaporated at 150° C. until dryness, whereby the solubility is determined from the weight of the sample before immersing and the residue amount in the stoppered bottle.

The standard for this determination is 2 w/w% or less.

In addition, since it is considered that, in this experiment, the decomposition character into water is a unfavorable phenomenon, the decomposition percentage is determined as including the solubility and the decomposition amount.

4) Resisting force for crushing

A slice having a diameter of 6 mm and a height of 12 mm is prepared and allowed to stand 24 hours under the conditions of room temperature of 37° C. and relative humidity of 100% and then, the resisting force for crushing is determined.

The determination is carried out with a Shimazu O-graph IS-5000 and with a cross-head speed of 0.5 mm per minute.

5) Slow-release of tannic acid from hardened product

A slice prepared in a similar way as used for determination of the decomposition degree is immersed in 50 ml of distilled water at 37° C. for 24 hours and then, the water in a stoppered bottle is taken as a solution for examination. This solution for examination, 5 ml, is treated with addition of 2 drops of a test solution of ferric chloride and subjected to a quantitative measurement with a colorimeter at 590 n, thereby presence or absence of tannic acid is confirmed.

6) Pathological observation with filling into a molar root canal of a grown dog

A molar dental pulp of a grown dog is extracted and then, without combination use a point such as guttapercha point, each cement or kneaded med of a root canal sealer is filled with pressure into a washed root canal and the crown part is filled and restored with use of glass-ionomer cement. With the passage of three months, a slice for polishing which was not decalcificated was prepared by tooth extraction followed by setting with a 10% aqueous formalin solution. After the H-E coloring treatment, a pathological observation was carried out.

Results are shown in Table 8.

TABLE 8

| | Powder to liquid ratio (g/ml) | Flow (mm) | Time for hardening | Decomposition percentage (w/w %) | Resisting force for crushing (kgf/cm$^2$) | Slow-release of tannic acid | Remark on pathological sample |
| --- | --- | --- | --- | --- | --- | --- | --- |
| example 62 | 2.0 | 25 | 51 min. | 1.21 | 230 | presence | closing of apical hole with fibrous tissue |
| example 63 | 2.0 | 35 | 3 hr. | 1.63 | 120 | presence | closing of apical hole with fibrous tissue |
| example 64 | 2.0 | 38 | 8 hr. | 1.83 | 105 | presence | closing of apical hole with fibrous tissue and calcification of directly down part |
| example 65 | 2.0 | 36 | 12 hr. | 0.95 | 110 | presence | closing of apical hole with fibrous tissue and calcification of directly down part |
| example 66 | 2.0 | 28 | 48 hr. | 1.53 | 100 | presence | closing of apical hole with fibrous tissue and calcification of directly down part |
| example 67 | 2.0 | 39 | 12 hr. | 0.33 | 160 | absence | calcification of apical hole and closing of apical hole with growth of cement |
| example 68 | 2.0 | 31 | 40 min. | 0.91 | 90 | absence | closing of apical hole with fibrous tissue and calcification of directly down part |
| example 69 | 2.0 | 33 | 2 hr. | 0.83 | 105 | absence | calcification of root canal and closing of apical hole with growth of cement |
| example 70 | 2.0 | 30 | 45 min. | 0.90 | 80 | absence | closing of apical hole with fibrous tissue |
| example 71 | 2.0 | 27 | 3 hr. | 0.72 | 100 | absence | calcification of root canal and closing of apical hole with growth of cement |
| example for comparison 10 | 4.0 | 22 | 30 min. | 0.49 | — | absence | confirmation of local inflammatory megakaryocyte in apical hole |
| example for comparison 11 | 4.0 | 30 | 20 min. | 0.71 | — | absence | confirmation of pus blister in gum around apical hole |
| example for comparison 12 | 5.0 | 40 | 2 hr. | 0.90 | 110 | absence | confirmation of pus blister in gum around apical hole |

As seen in Table 8, although there is no problem in the examples, inflammation and pus blisters were confirmed in the examples for comparison.

In addition, concerning each of the hardening materials in the examples and the examples for comparison shown above as well as in the examples for comparison 13~15 described below, the powder and liquid were both treated with sterilization, mixed, and kneaded for about 1 minute whereby the mud obtained was treated with an initial hardening during only the time for hardening of each hardening material to make a cylindrical piece having a diameter of 4 mm and a length of 10 mm. These pieces were inserted into the femoral bone shaft of a grown dog by making a drill hole which is just 0.2 ~0.3 mm larger than said pieces and each hardening material was buried for 2, 4, and 6 weeks. Then, for each hardening material, the slices for polishing which were decalcificated and not decalcificated were prepared. The slice decalcificated was colored with the H-E coloring and with toluidine blue to carry out a pathological observation, and the slice for polishing not decalicificated with colored with the H-E coloring to do that. Furthermore, concerning the force for fixing with a bone tissue, the force for cutting was measured according to a pushing-out method with 0.1 mm/min. of a cross-head speed, by using a universal test machine of a rod cell type. Results are shown in Table 9.

TABLE 9

| | Pathological remark | Fixing force with bone tissue |
|---|---|---|
| example 1 | After 2 weeks, direct bond with a bone was in part observed, but slight cell wetness of a circle shape was found. After 4 and 6 weeks, inflammation symptoms gradually disappeared and at this part bone formation gradually increased in amount. | After 6 weeks: 30 kgf/cm$^2$ |
| examples 5, 7, 10, 19, 21, 22, 25, and 35 | Inflammation reaction was not observed. After 2 weeks, direct bond formation with a bone began. After 4 weeks, a number of bone cells existed around an interface with the bone tissue. After 6 weeks, the bone increased in amount. | After 6 weeks: 70 kgf/cm$^2$ |
| examples 2 and 38 | Almost no inflammatory reaction. After 4 weeks, direct bond formation with a bone had already begun and at an interface bone cells existed. | After 6 weeks: 45 kgf/cm$^2$ |
| examples 12, 20, 40, 42, 45, 47, 48, 50, 51, 52, and 54 | Almost no inflammatory reaction. After 4 weeks, direct bond formation with a bone had already begun and at an interface bone cells existed. | After 6 weeks: 30 kgf/cm$^2$ |
| examples for comparison 2 and 4 | Same to example 1 | After 6 weeks: 20 kgf/cm$^2$ |
| example for comparison 13 | After 2 weeks, a connective tissue with a bone tissue existed. Inflammatory reaction and cell wetness were found. After 4 and 6 weeks, was the same. | After 6 weeks: 1 kgf/cm$^2$ |
| example for comparison 14 | After 2 weeks, a connective tissue with a bone tissue existed. Slight inflammatory reaction and cell wetness were found. After 6 weeks, although bond formation with a bone tissue was in part observed, the parts where connective tissue existed was major. | After 6 weeks: 5 kgf/cm$^2$ |
| example for comparison 15 | Almost no inflammatory reaction. A connective tissue with a bone tissue existed and there is no bond part with a bone. | After 6 weeks: 0.5 kgf/cm$^2$ |

EXAMPLE FOR COMPARISON 13

Used was a hardening material composed of the combination of a powder agent which contained 100% of α-TCP, with a setting solution (a liquid agent) composed of 40% of polyacrylic acid.

EXAMPLE FOR COMPARISON 14

Used was a hardening material composed of combination of a powder agent which contained 61% of α-TCP, 36% of 4CP, and 3% of HAp, with a setting solution (a liquid agent) which was prepared by dissolving polyacrylic acid and citric acid in their respective proportion of 17% and 30% into water.

EXAMPLE FOR COMPARISON 15

Used was bone cement in a PMMA series commercially available from Howmedica Co., Ltd. under the tradename Surgical Simplex.

As seen in Table 9, the fixing force with a bone tissue in the examples was higher than that in the examples for comparison and, in particular, the examples in which aterocollagen was used were better.

INDUSTRIAL APPLICABILITY

The hardening material relating to the present invention can be used as a root canal sealer, cement and a filling agent for dental use, bone cement and a filling agent, and the like.

What is claimed is:

1. A hardening material for medical and dental use, comprising calcium phosphate powder containing at least one of α-tricalcium phosphate and tetracalcium phosphate and at least one compound selected from tannin and tannin derivatives and at least one compound selected from collagen and collagen derivatives as hardening adjusters.

2. A hardening material for medical and dental use, comprising calcium phosphate powder containing at least one of α-tricalcium phosphate and tetracalcium phosphate and at least one compound selected from collagen and collagen derivatives and at least one organic aid as hardening adjusters.

3. A hardening material for medical and dental use, comprising calcium phosphate powder containing at least one of α-tricalcium phosphate and tetracalcium phosphate, as a hardening material, at least one compound selected from tannin and tannin derivatives, at least one compound selected from collagen and collagen derivatives, and at least one organic acid.

4. A hardening material for medical and dental use as claimed in claims 1, 2 or 3, wherein the collagen and the collagen derivative convert into fibrils under a physiological condition.

5. A hardening material for medical and dental use as claimed in claim 4, wherein the collagen and the collagen derivative require time longer than 8 minutes for conversion into fibrils under a physiological condition.

6. A hardening material for medical and dental use comprising α-tricalcium phosphate powder, tannic acid, at least one organic acid as a hardening adjuster, and water, the total amount of the organic acid and tannic acid being 40~48% by weight of said water, organic acid and tannic acid, said organic acid being selected from citric acid and malonic acid, the mutual proportion of the citric acid, malonic acid, and tannic acid is, relative to 100 parts by weight of a total of the three acids, 60~90 parts by weight for citric acid, 0~35 parts by weight for malonic acid, and 30 parts or less by weight for tannic acid, with the proviso that when the malonic acid is 0 part by weight, the citric acid is 70~89 parts by weight and the tannic acid 30~11 parts by weight.

7. A hardening material for medical and dental use comprising α-tricalcium phosphate powder, tannic acid, at least one organic acid as a hardening adjuster, and water, the total amount of organic acid and tannic acid being 40~48% by weight of said water, organic acid and tannic acid, said organic acid being selected from citric acid and malic acid, the proportion of the citric acid, malic acid, and tannic acid, relative to 100 parts by weight of a total of the three acids, being 0~65 parts by weight for citric acid, 20~90 by weight for mallic acid, and 15 parts or less for tannic acid.

8. A hardening material for medical and dental use comprising α-tricalcium phosphate powder, organic acids as hardening adjusters, and water, the organic acids being 40~48% by weight of the organic acids and said water, said organic acids being citric acid and malonic acid, and the proportion of citric acid and malonic acid being, relative to 100 parts by weight of the total of these two acids, 65~90 parts by weight citric acid and 10~35 parts by weight malonic acid.

* * * * *